United States Patent
Pugh

(10) Patent No.: US 6,908,008 B2
(45) Date of Patent: Jun. 21, 2005

(54) TEST DEVICE WITH MEANS FOR STORING AND DISPENSING DIAGNOSTIC STRIPS

(75) Inventor: Jerry T. Pugh, Mountain View, CA (US)

(73) Assignee: LifeScan, Inc., Milpitas, CA (US)

(*) Notice: Subject to any disclaimer, the term of this patent is extended or adjusted under 35 U.S.C. 154(b) by 52 days.

(21) Appl. No.: 10/029,525

(22) Filed: Dec. 21, 2001

(65) Prior Publication Data

US 2003/0116583 A1 Jun. 26, 2003

(51) Int. Cl.[7] .................................................. A24F 27/14
(52) U.S. Cl. ..................................... 221/135; 221/232
(58) Field of Search ................................... 221/232, 247, 221/250, 267, 7, 268, 279; 206/817, 204, 569, 355; 422/63, 65, 99

(56) References Cited

U.S. PATENT DOCUMENTS

| | | | | |
|---|---|---|---|---|
| 3,393,831 A | * | 7/1968 | Stewart | 221/232 |
| 4,190,420 A | | 2/1980 | Covington et al. | |
| 4,817,820 A | | 4/1989 | Heiland | |
| 4,911,344 A | * | 3/1990 | Kahler | 221/135 |
| 5,489,414 A | * | 2/1996 | Schreiber et al. | 422/64 |
| 5,510,266 A | | 4/1996 | Bonner et al. | |
| 5,526,120 A | | 6/1996 | Jina et al. | |
| 5,575,403 A | | 11/1996 | Charlton et al. | |
| 5,630,986 A | | 5/1997 | Charlton et al. | |
| 5,665,310 A | * | 9/1997 | Augstein | 422/66 |
| 5,846,490 A | * | 12/1998 | Yokota et al. | 422/66 |
| 2002/0057993 A1 | | 5/2002 | Maisey et al. | |
| 2002/0076349 A1 | | 6/2002 | Aitken et al. | |
| 2003/0089730 A1 | | 5/2003 | May et al. | |

FOREIGN PATENT DOCUMENTS

| | | |
|---|---|---|
| DE | 42 05 805 | 9/1993 |
| EP | 0 304 838 A | 3/1989 |
| EP | 0 308 770 A | 3/1989 |
| WO | WO 94/10558 | 5/1994 |
| WO | WO 98/47007 | 10/1998 |

OTHER PUBLICATIONS

Website//www.accessdata.fda.gov/scripts/cdrh/cfdocs/cf-PMN/PMN.CFM?id=58028 (Sep. 15, 2003).
Description of INTEGRA Blood Glucose Monitoring System.
ACCU–CHEK advertisement; Dec. 4, 2001.

* cited by examiner

*Primary Examiner*—Kenneth Noland
(74) *Attorney, Agent, or Firm*—Susan Tall; Bozicevic, Field & Francis LLP

(57) ABSTRACT

The invention provides a substantially moisture-proof, airtight apparatus for both dispensing a plurality of diagnostic test strips and testing a biological fluid dispensed onto the strip. One strip may be advanced for use in testing using a single, translational movement.

12 Claims, 22 Drawing Sheets

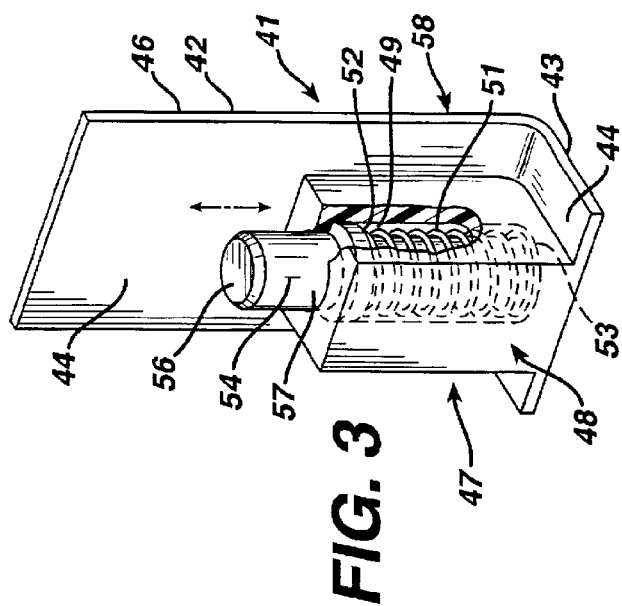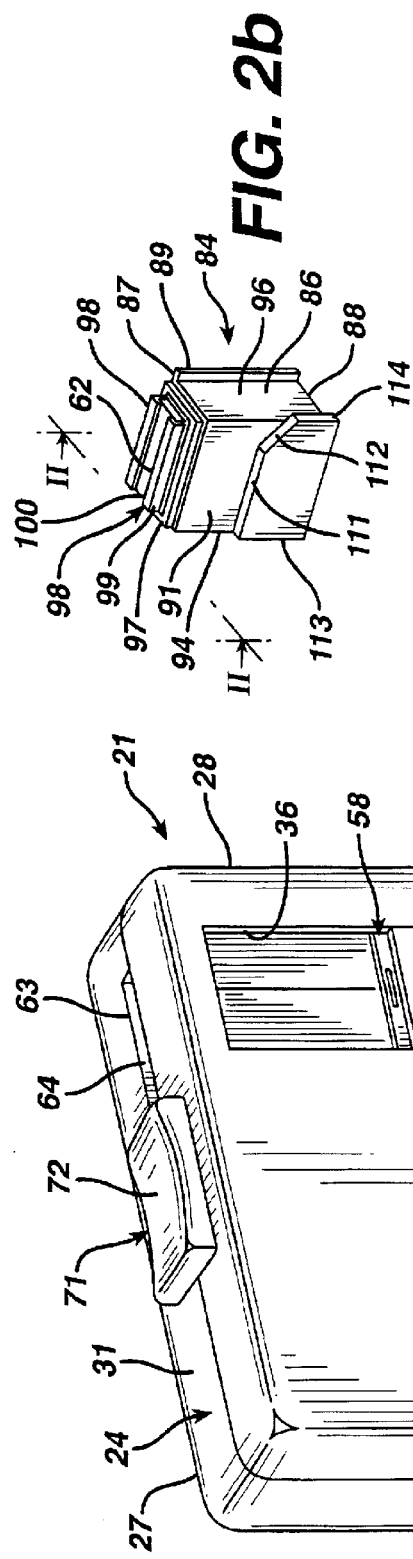

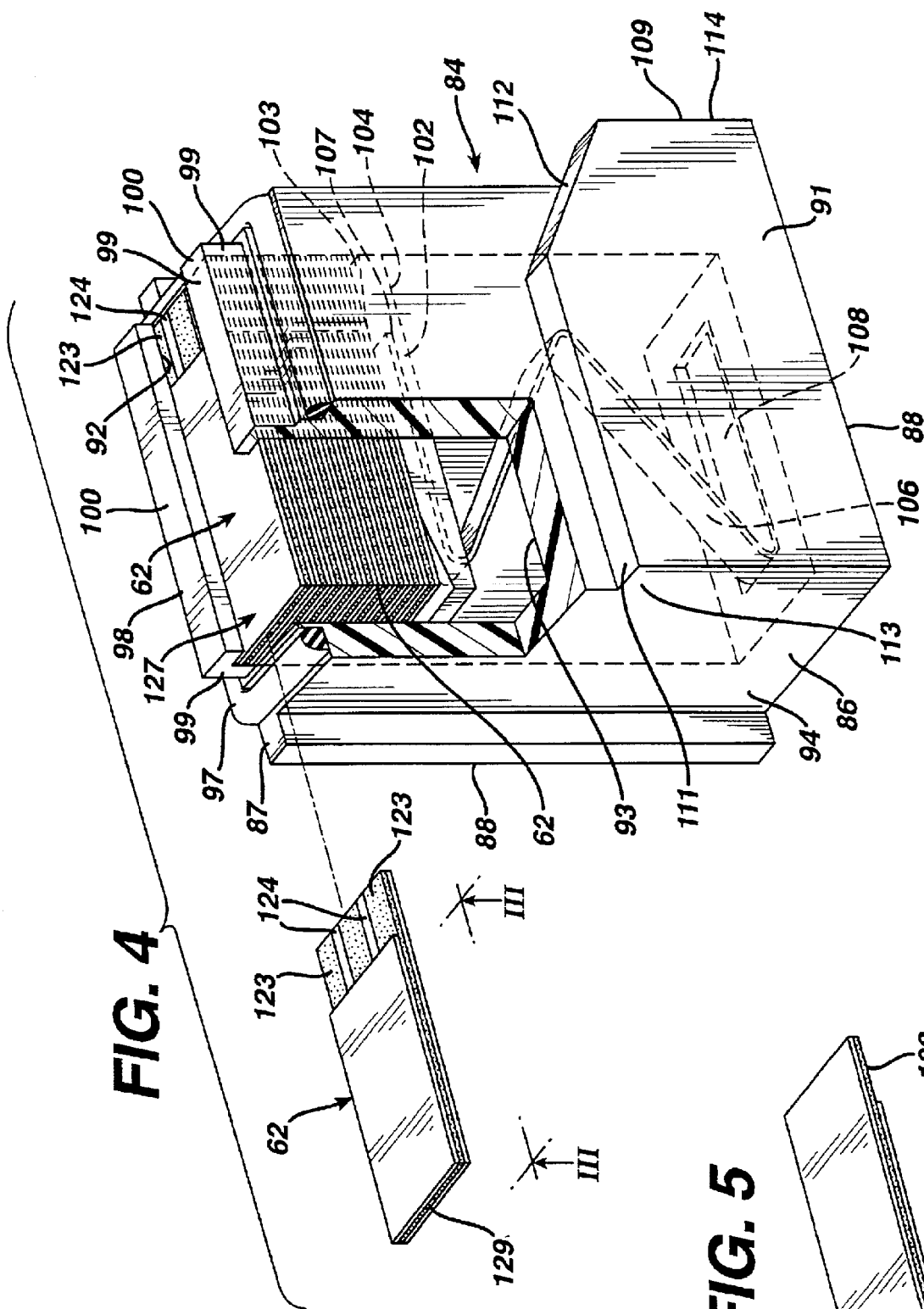
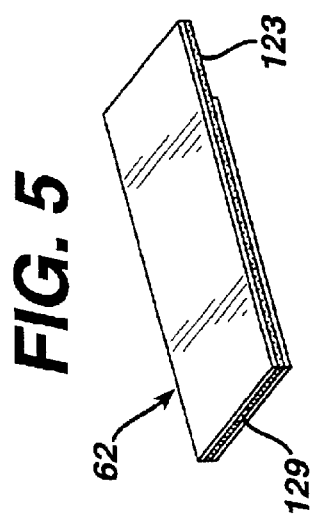
FIG. 4
FIG. 5

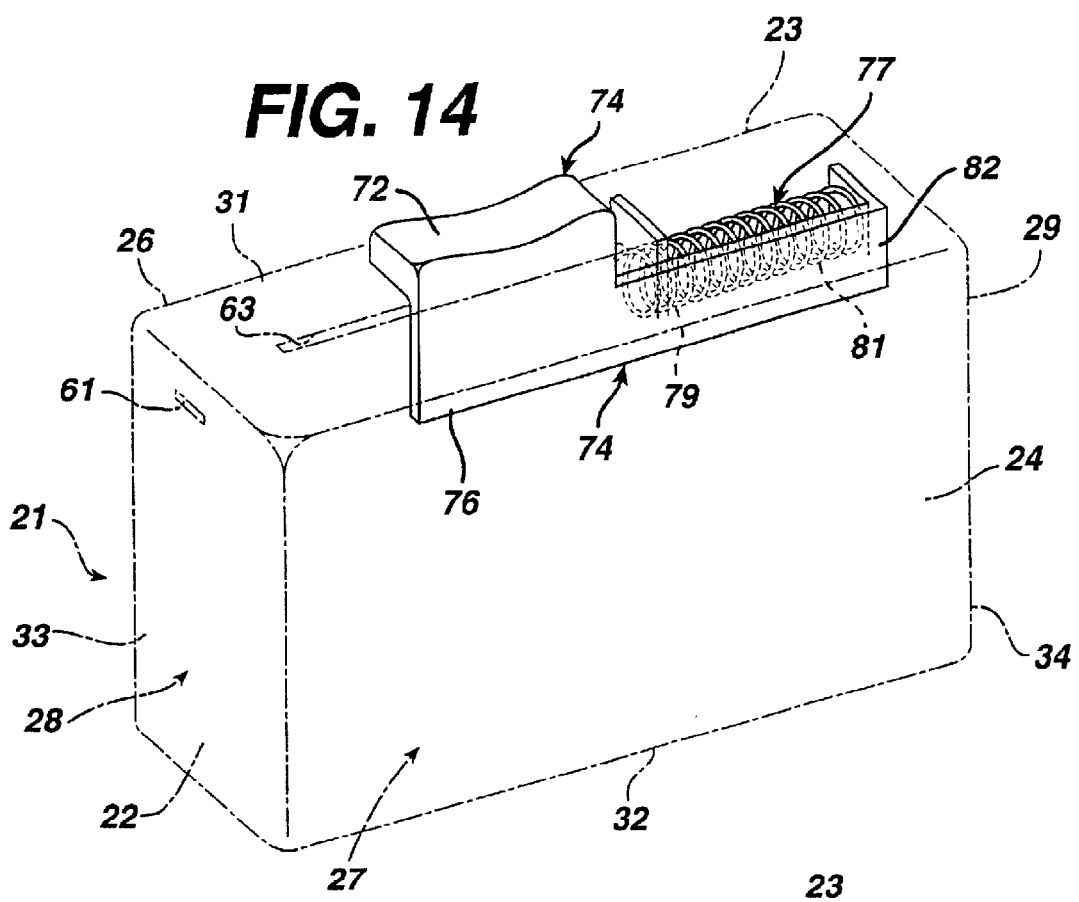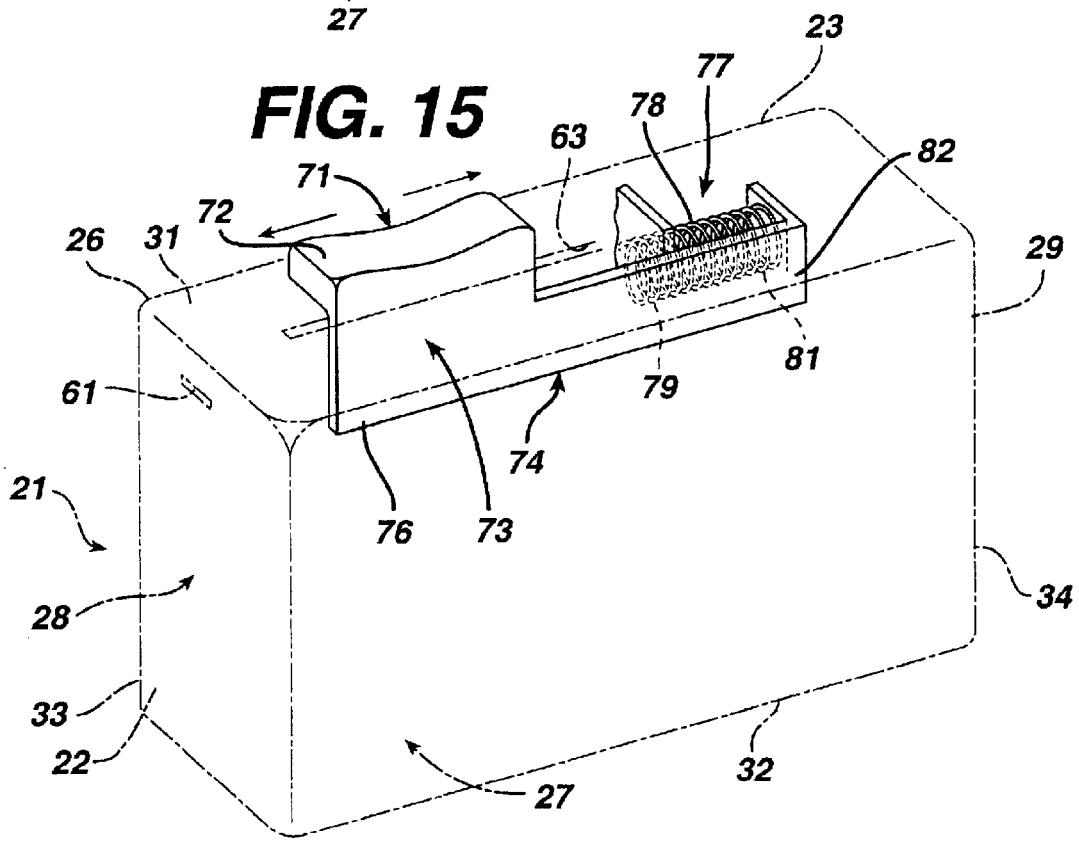

TEST DEVICE WITH MEANS FOR STORING AND DISPENSING DIAGNOSTIC STRIPS

FIELD OF THE INVENTION

The invention relates to devices for testing biological fluids. In particular, the invention provides an apparatus for testing biological fluids which also stores and dispenses diagnostic test strips.

BACKGROUND OF THE INVENTION

Apparatuses and methods for measuring components of biological fluids as well as test strips for use in such devices are well known. Typically, the test strips are stored in a disposable container that is separate from the apparatus that measures the fluid component of interest. A test strip is removed from the container, a sample of fluid is dispensed onto the strip, and the strip is inserted into a photometric or electrochemical meter for analysis of the desired component. After analysis is completed, the test strip is extracted from the meter and the strip disposed.

Ease of use of hand held test strip dispensers and meters is important particularly for those dispensers that will be used by persons with diminished hand-eye coordination or finger sensation. For example, persons with diabetes typically have either or both impaired vision and diminished fingertip sensation. Such persons must use test strips and meters to test their blood glucose levels a number of times a day. However, the typical test strip is only several millimeters in width and length and, thus, difficult to manipulate. Additionally, conventional strips are typically packed in small, cylindrical containers from which it is difficult to easily extract a single strip.

BRIEF DESCRIPTION OF THE DRAWINGS

FIG. 2a is a perspective view of the apparatus of FIG. 1 depicting a panel of the apparatus in an open position.

FIG. 2b is a perspective view of a cartridge for use in the apparatus of FIG. 2a.

FIG. 3 is an enlarged view of an apparatus within the dispenser of FIG. 2 taken along the line I—I.

FIG. 4 is an enlarged view of the cartridge of FIG. 2b with a partial cut-away taken along the II—II line and showing a strip retained in the cartridge.

FIG. 5 is a perspective view of a test strip useful in the apparatus of the invention, which view is taken along the III—III line of FIG. 4.

FIG. 14 is a perspective view of the apparatus of FIG. 1 showing the spring mechanism of the slide member in the first position.

FIG. 15 is a perspective view of the apparatus of FIG. 14 showing the spring mechanism and slide member in the second position.

DETAILED DESCRIPTION OF THE INVENTION AND PREFERRED EMBODIMENTS

The invention provides a substantially moisture-proof, air-tight apparatus for both dispensing diagnostic test strips and testing a biological fluid dispensed onto the strip. The apparatus of the invention, holds a plurality of test strips and is opened and one strip is advanced for testing using a single, translational movement. Thus, the apparatus is both easily utilized in dispensing a single diagnostic test strip and provides a convenient means for storing test strips and testing fluids using the strip.

In one embodiment, the invention provides an apparatus comprising, consisting essentially of, and consisting of: a.) dispenser comprising, consisting essentially of, and consisting of: i.) a housing having a chamber; ii.) a means for retaining a plurality of test strips in a substantially moisture-proof, and air-tight first position; iii.) a means for opening the chamber and moving one of the plurality of test strips translationally from a first position inside of the chamber to a second position at least partially outside of the chamber, wherein the opening of the chamber and moving of the one test strip is achieved by single mechanical motion; and b.) an analyzing means.

Figure 1:
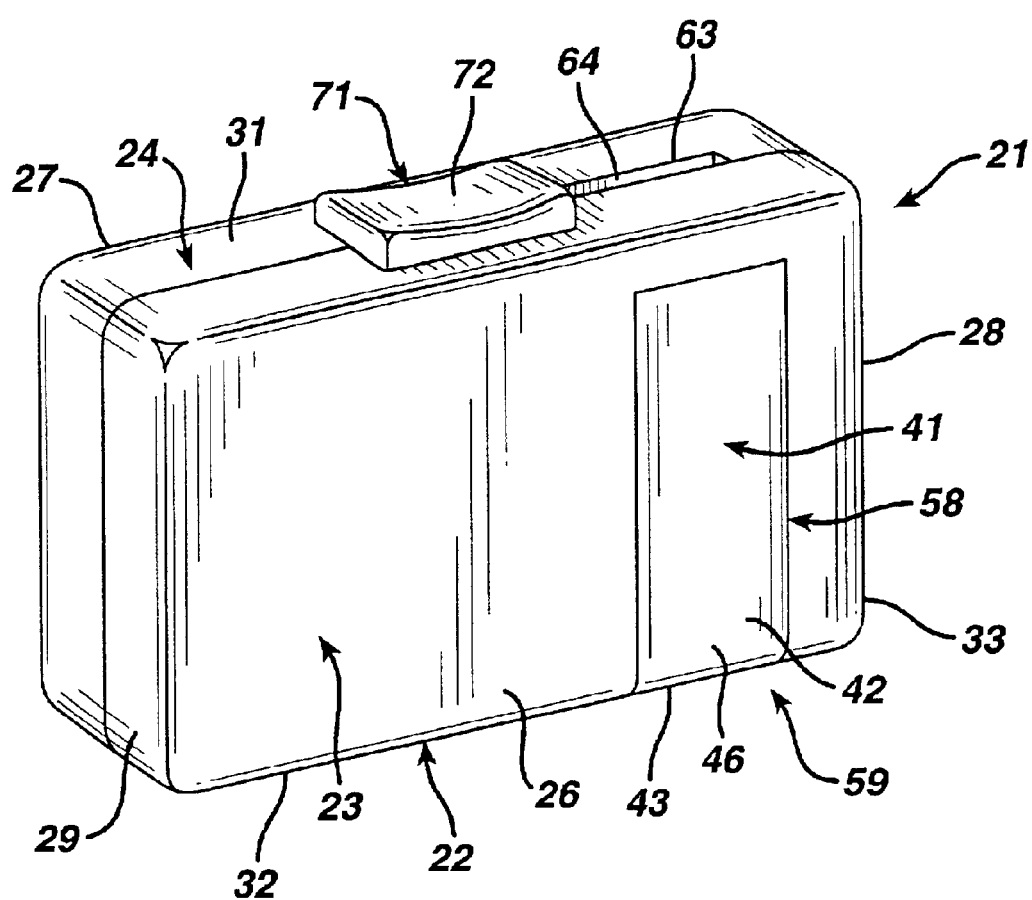
FIG. 1 is a perspective view of an embodiment of an apparatus of the invention.

Referring to FIG. 1, apparatus 21 of the invention is shown having housing 22. Preferably housing 22 has a substantially rectangular shape, as shown, with side walls 28 and 29, front and rear walls 26 and 27, respectively, top 31 and bottom 32. More preferably, housing 22 has right and left halves 23 and 24, respectively, secured to one another by any convenient securing means including, without limitation, by screws, use of complementary inserts, adhering means, or the like and combinations thereof. Housing 22 preferably is size and shaped so that it may be comfortably held in a user's hand.

Figure 9:
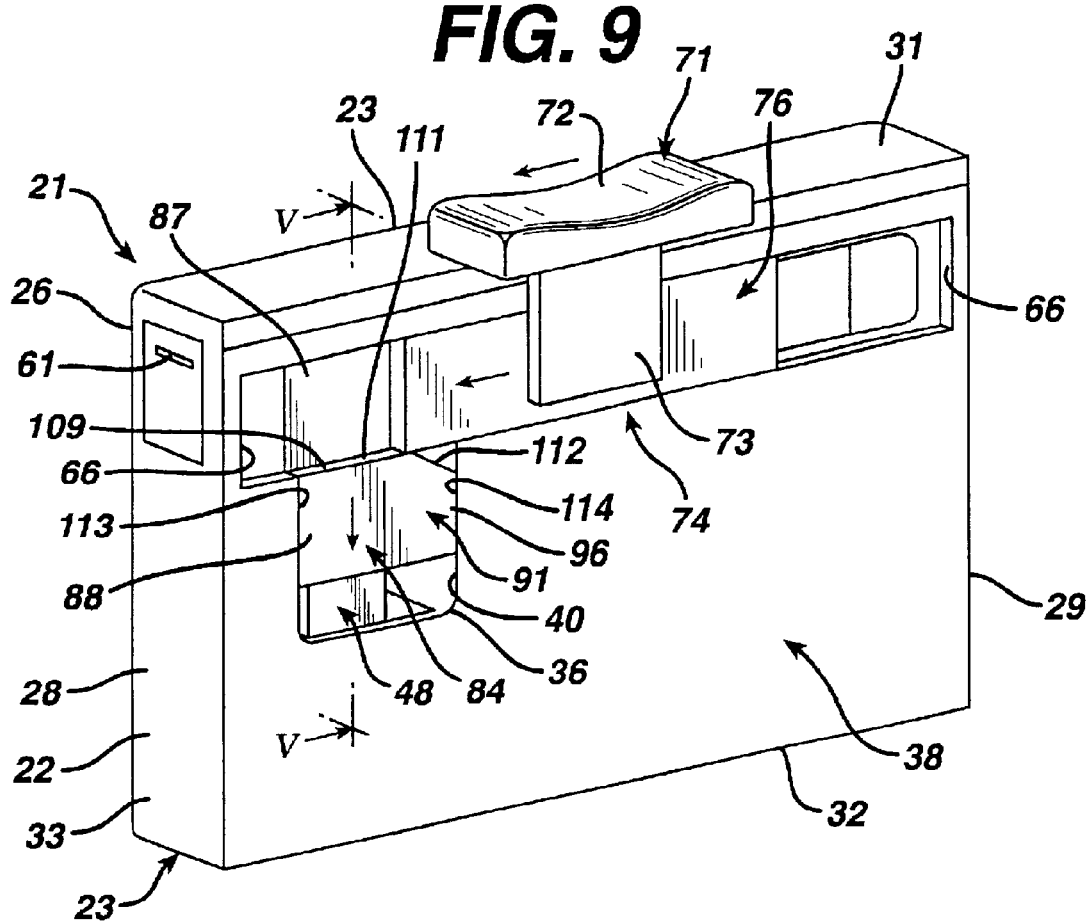
FIG. 9 is a perspective view of the apparatus of FIG. 1 showing the slide member and cartridge between the first and a second position.

Housing 22 is provided with chamber 36 therein and as depicted in FIG. 2. Medial wall 38 constitutes the innermost border of right half 23. Medial wall 38 has an opening 40 therethrough, shown in FIGS. 6, 9 and 12.

Right half 23 is provided with a panel 41 through which chamber 36 may be accessed by the user. Panel 41 has face and bottom segments 42 and 43, respectively, each having inner and outer surfaces 44 and 46. Panel 41 is shown in a closed position 59 in FIG. 1. Panel 41 is constructed to be movable from a closed to an opened position by any convenient means. For example and preferably, as shown in FIG. 2, panel 41 my be slidably movable. Alternatively, panel 41 may be hingedly affixed to housing 22.

Inner surface 44 of panel 41 has urging means 47, shown in FIG. 3. Urging means 47 includes casing 48 that is preferably formed integral with inner surface 44. Casing 48 is configured to fit within right half 23, for example in a cylindrical or rectangular configuration, and has hollow core 49 therein. Hollow core 49 is sized and shaped to retain flexible element 51 therein, as shown in FIG. 3. Flexible element 51 may be any element capable of holding cartridge 84 against sealing member 97 against circumferential collar 101. Preferably, flexible element 51 is a metal spring.

Bottom 53 of flexible element 51 is seated against inner surface 44 within core 39. Top extremity 52 of flexible element 51 carries a plunger element 54 that is provided with top and bottom ends 56 and 57, respectively. Bottom end 57 is appropriately sized so that it can be secured to top extremity 52 by being frictionally retained therein, or affixed thereto.

Figure 6:
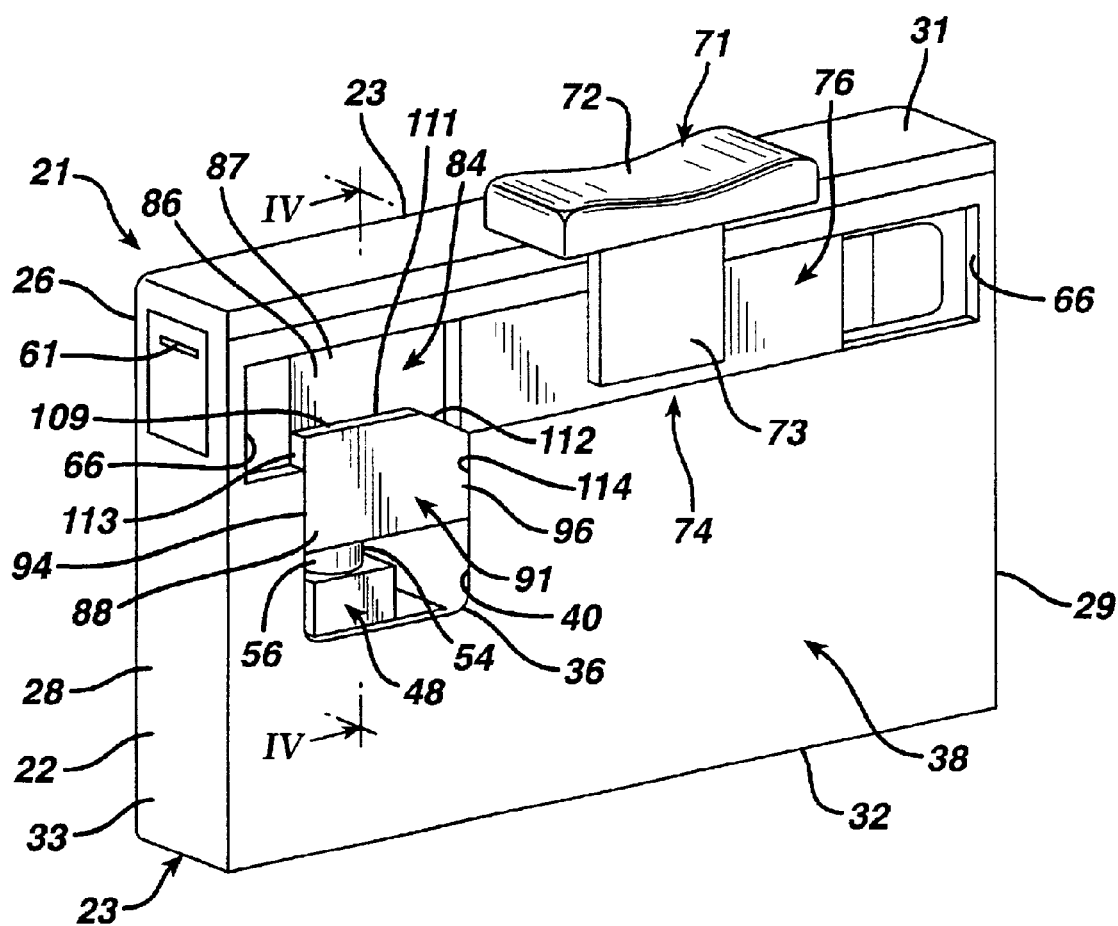
FIG. 6 is a perspective view of the right half of the apparatus of FIG. 1 showing a slide member and cartridge in a first position.
Figure 7:
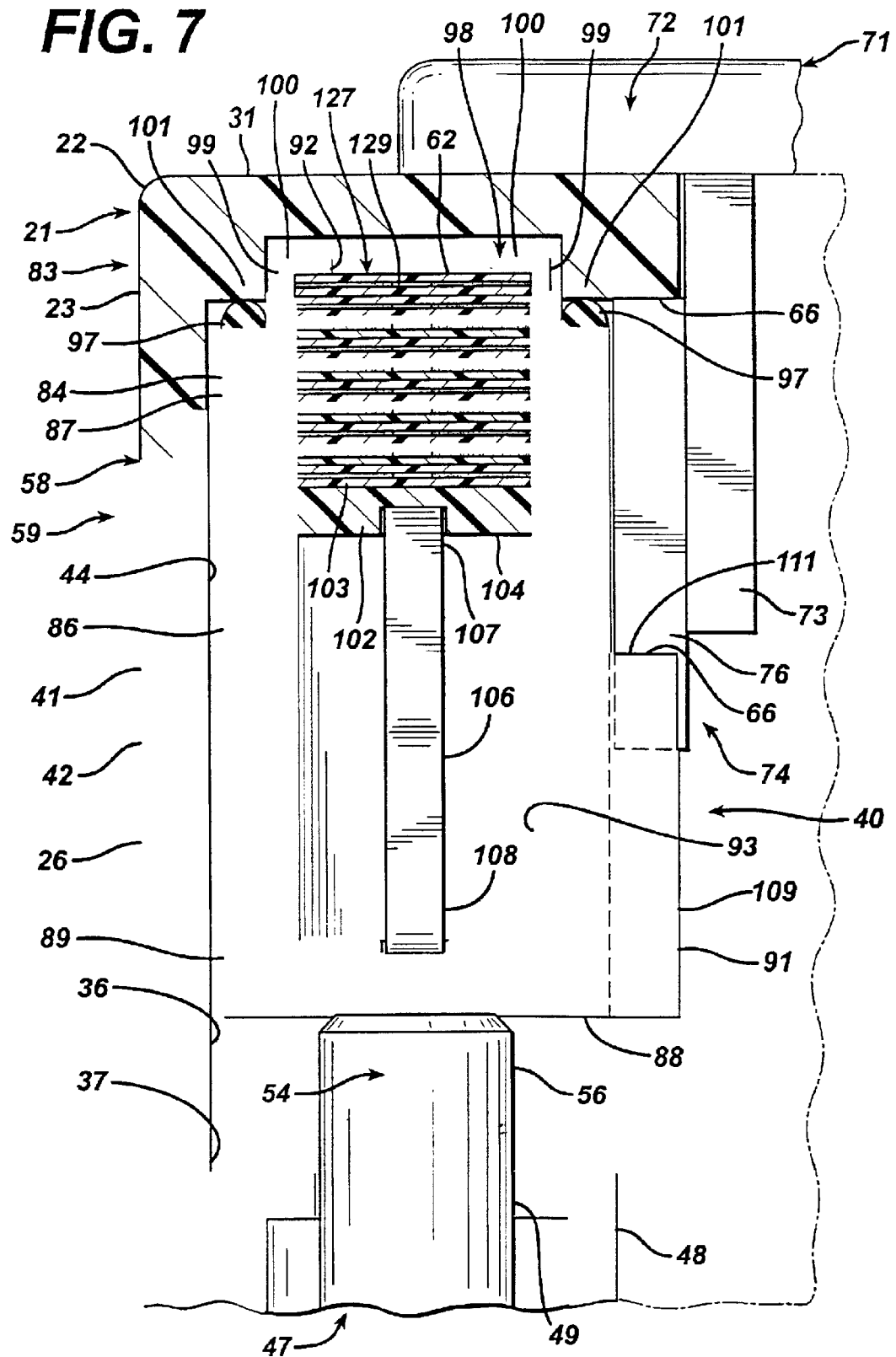
FIG. 7 is a perspective view taken along the line IV—IV of FIG. 6.

As shown in FIG. 6, front end 33 of housing 22 is provided with dispensing outlet 61 which is preferably transversely situated at an appropriate distance below top 31 to permit the top of cartridge 84 to fit inside housing 22, for example as shown in FIG. 7. Slot 61 is sized to accommodate a conventional diagnostic test strip, such as strip 62 shown in FIGS. 4 and 5. Top 31 of housing 22 also is provided with a slide slot 63, shown in FIGS. 1 and 2, that is preferably formed by providing left half 24 with a small cutout segment 64 that indents.

As shown in FIG. 6, the upper portion of medial wall 38 of right half 23 is subtended by a shallow track or groove 66 running transversely the length of medial wall 38, except for its traverse of opening 40. Preferably, groove 66 does not run the entire length of the wall, but ends so that the slot is closed at the front and rear walls 33 and 34, respectively, and the inside of the dispenser is not exposed to the environment.

Housing 22 carries slide member 71 adapted to move, or slide, along slide slot 63. Slide member 71 has tab portion 72 sized and configured to be engaged and actuated by the finger of an operator using apparatus 21, as hereinafter described. Preferably, the top tab 72 is conventionally knurled to optimize gripping by the user's finger.

As shown in FIGS. 6 and 7, slide member 71 is provided with tongue portion 73, preferably constructed integral to tab 72 and extending from the underside of tab 72 at substantially a right angle. Tongue 73 is sized and configured so that, when the underside of tab 73 is slidably disposed upon top 31, tongue 73 extends downwardly through slide slot 63. Tongue 73 is of an appropriate length so that it extends downwardly approximately to, but not below, the lower border of track 66. The width of tongue 73 determines the range within which slide member 71 may be moved along top portion 31 and is of a width less than the length of slide slot 63. Formed integrally with, or secured to, tongue 73 is cam member 76 of cam means 74. Cam member 76 preferably is rectangular in configuration and sized to engage track 66 by being slidably disposed in, and substantially flush, therewith. The length of cam member 76 is appropriately greater than the length of opening 40 in medial wall 38 of right half 23.

As shown in FIGS. 14 and 15, slide member 71 is coupled to means for urging 77, which means serves to urge slide member 71 rearwardly along slot 63. Urging means 77 may be any suitable element, such as metal spring 78 as shown, and has front and rear extremities 79 and 81. Front extremity 79 of spring 78 is secured to the underside of top 31 with rear extremity 81 being secured to rear portion of cam member 76. Cam member 76 is provided with a rearward extension 82 to which rear extremity 81 may be coupled. One ordinarily skilled in the art will recognize that, alternatively, spring 78 may be secured to any other appropriate portion of slide member 71, such as tongue 73.

The dispenser of the invention also is provided with means for retaining a plurality of conventional diagnostic test strips in a substantially moisture-resistant and air-tight first position within chamber 36. Retaining means 83, shown in FIGS. 7 and 10, has therein a cartridge, or cassette, 84 that has a casing, or housing, 86. Casing 86 has top and bottom ends 87 and 88, respectively, right and left faces 89 and 91, respectively, and an opening 92 through the topmost portion of top end 87. Opening 92 opens into internal cartridge chamber, or compartment, 93 extending from top 87 to bottom end 88. Bottom end 88 is closed as seen best in FIG. 4. Cartridge chamber 93 is sized and configured to accommodate a plurality of diagnostic test strips 62 and is preferably rectangular in cross-section.

Figure 10:
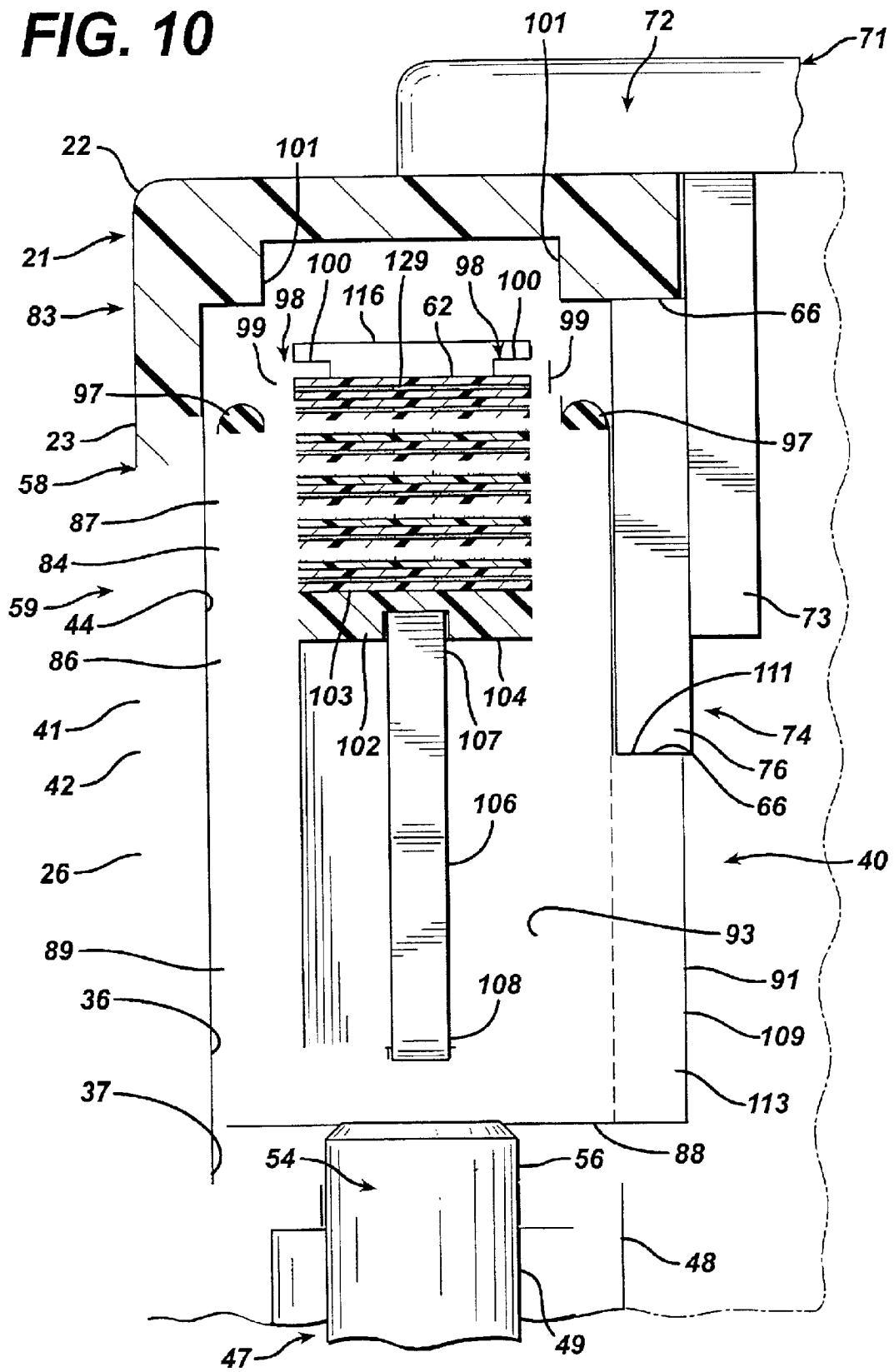
FIG. 10 is a view along line V—V of FIG. 9.

Casing 86 is removably disposed within chamber 36 with the front and rear faces, or walls, 94 and 96 of cartridge 84 facing front and rear walls 28 and 29, respectively, of housing 22, as seen in FIG. 6. In this regard, casing 86 is preferably substantially rectangular in cross-section and, in conjunction with cartridge chamber 93, extends along a longitudinal axis from front to rear faces 94 and 96. In addition, the cross-sectional length of casing 86 is preferably less than the width of window 40. Shown in FIGS. 7 and 10 is sealing member 97 having a semi-circular cross-section mounted and secured to the top end or rim 87 of casing 86 in any convenient manner, as for example being glued thereupon.

Top end 87 of casing 86 also is provided with right and left strip guide rails 98. Each of rails 98 has upright and transverse legs 99 and 100. Upright leg 99 of rail 98 preferably is formed integral to and is a split thickness extension of right and left faces 89 and 91. In this regard, upright leg 99 is inset from sealing member 97 so that the inner surface of upright leg 99 is determined by inner surface of right and left faces 89 and 91, as shown in FIG. 4. Preferably, transverse leg 100 extends inwardly towards cartridge chamber 93. The distance between the underside of transverse leg 100 and the top of sealing member 97 is larger than the thickness of strip 62, but smaller than twice the thickness of strip 62.

Retaining means 83 further includes a sealing surface having an inwardly extending circumferential collar 101 carried by and preferably formed integral with the inner face of top 31 of housing 22. When cartridge 84 is disposed within chamber 36, sealing member 97 seats against collar 101 by the action of plunger 54 acting upwardly on the bottom of cartridge 84, as hereinafter described. Thus, collar 101 has substantially the same width as sealing member 97 and extends downwardly from the uppermost portion of the inner face of top 31 for a distance corresponding to at least the length of upright leg 99 of guide rail 98, as shown in FIGS. 7 and 10.

Cartridge 84 includes means for biasing the plurality of diagnostic test strips 62 retained therein towards opening 92. An optional, but preferred, support plate 102 having upper and lower surfaces 103 and 104 and dimensions approximating those of strip 62 is disposed in cartridge chamber 93. A spring means, that may be a flat spring as shown in FIG. 7, 106 having upper and lower extremities 107 and 108, respectively, is secured within chamber 93. Preferably, spring means 106 is Z-shaped with lower extremity 108 being secured to the inner face of bottom end 88 of casing 86 within chamber 93, upper extremity 107 being conventionally secured to lower face 104 support plate 102. When retained within cartridge chamber 93, a stack of test strips 62 rests upon upper surface 103 whereby they are biased upwardly by spring means 106 towards opening 92 with uppermost strip 62 resting upon the underside of transverse leg 100, as shown in FIG. 4.

Also as shown in FIG. 4, left face 91 of cartridge 84 carries cam following lip 109, preferably integral thereto. Lip 109 is a widened portion of left of left face 91 and has transverse and inclined legs, or segments, 111 and 112, as well as front and rear upright segments 113 and 114, respectively. The top of front upright segment 113 meets and is continuous with the front end of transverse leg 111. Transverse leg 111 extends rearwardly and meets and is continuous with the front end of leg 112. Leg 112 extends rearwardly and is inclined inferiorly for an appropriate distance whereupon inclined leg 112 meets and is continuous with the top of rear upright segment 114. Cartridge 84 is sized and configured so that, when disposed within chamber 36 with spring 51 of urging means 47 in the fully depressed configuration, transverse leg 111 is aligned below and is in contact with the bottom edge of cam member 76 for operation as hereinafter described and shown in FIG. 12.

Figure 22:
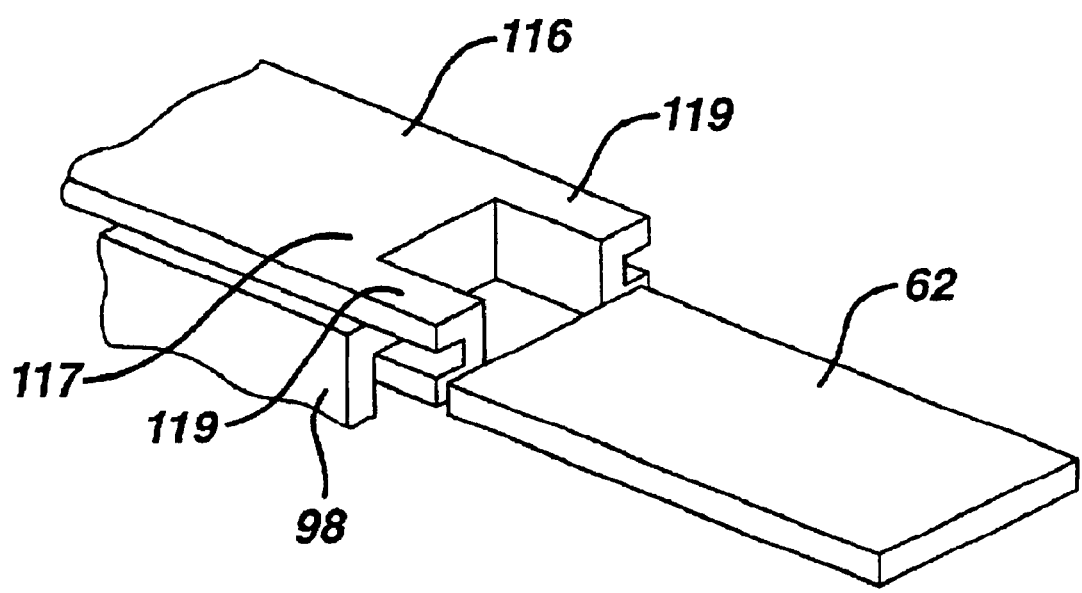
FIG. 22 is a perspective view of a portion of the apparatus of FIG. 1 and a strip.

Means for engaging moving strip 62 during operation of apparatus 21 is coupled to slide member 71 and cam means 74. A strip push member 116 is conventionally secured to the side of cam member 76, which faces wall 26 by providing a slot (not shown) in track 66 through which push member 116 extends toward right wall 26 of housing 22. Push member 116 preferably has a substantially I-beam configuration. The front extremity 117 of push member 116 is provided with at least two tines 119 extending longitudinally therefrom, as shown in FIG. 22.

Apparatus 21 additionally has an analyzing means for analyzing biological fluid dispensed onto strip 62, which analyzing means preferably primarily is situated in left half 24. Preferably, the analyzing means is any conventional electrochemical means useful for analyzing a fluid. Left wall 27 preferably incorporates means for powering the analyzing means as well as digital displays (not shown) for presenting results of measurements acquired during operation of the apparatus.

Figure 13:
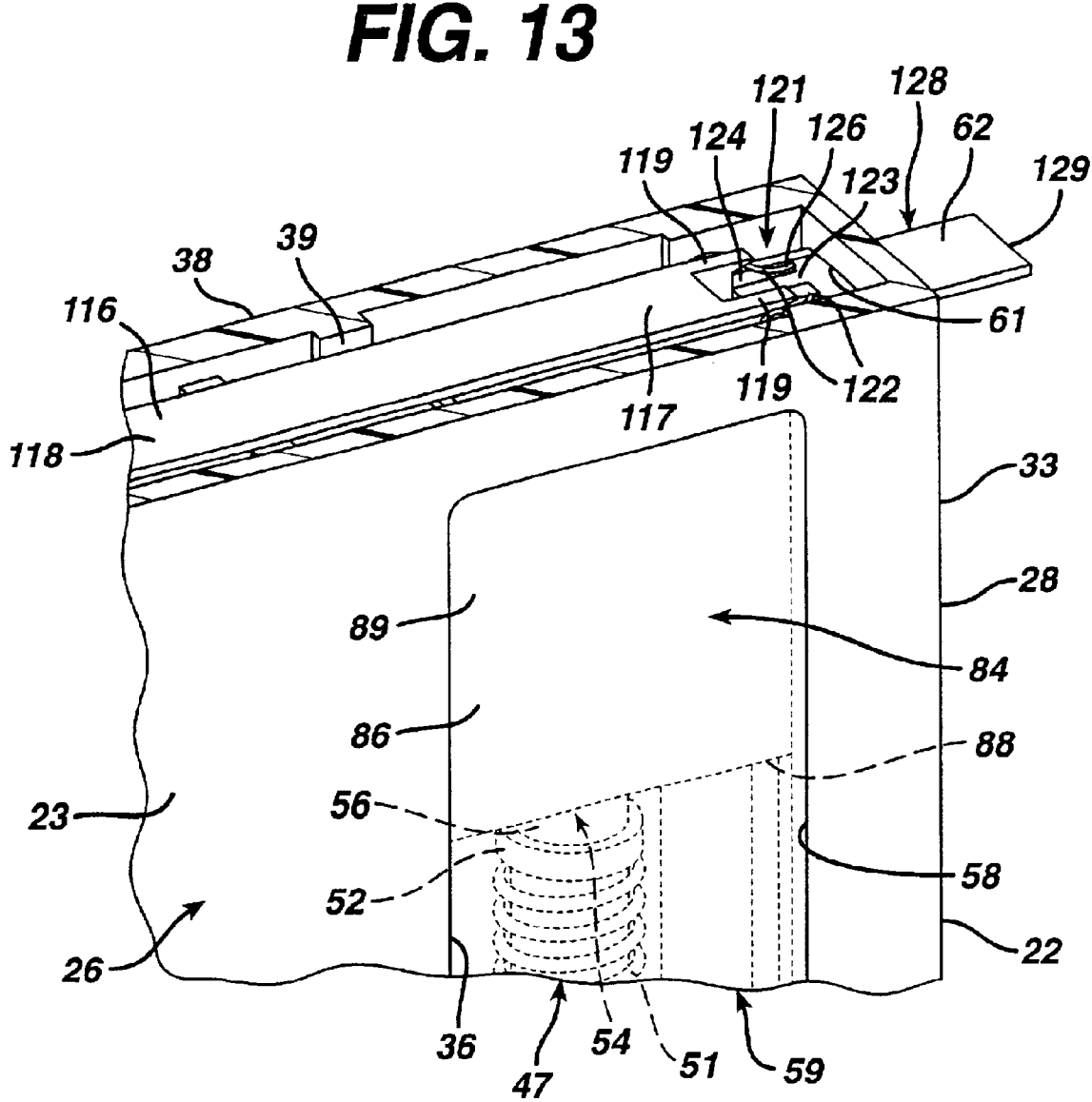
FIG. 13 is an enlarged view of the apparatus of FIG. 12 depicting the cartridge in the second position.

In a preferred example, working and reference electrodes 122 are mounted in an appropriate manner within housing 22 forward of cartridge 84 so that, when cartridge 84 is disposed in chamber 36 with spring means 51 fully compressed, at least a portion of contact segment 126 is coaxially aligned with the test strip electrodes of the uppermost strip 62 disposed in cartridge chamber 93 for coupling thereto during an operation, as shown in FIGS. 4, 5, and 13.

In order to operate apparatus 21, cartridge 84 as shown in FIG. 2b, is removed from a disposable, air- and fluid-tight wrapping (now shown). The user accesses chamber 36 of apparatus 21 through panel door 41. In the embodiment shown in FIG. 2, door 41 is moved downwardly into the fully open configuration 60, cartridge 84 is then inserted into chamber 36 and, using mating means 58, door 41 is moved upwardly into the fully closed position 59, shown in FIG. 1. During closure of door 41, as top of plunger 56 contacts bottom end 88 of cartridge 84 and is increasingly directed upwardly with respect thereto, spring 51 resists compression which, in turn, urges cartridge 84 upwardly until, when door 41 is fully closed, sealing member 97 of cartridge housing 86 seats firmly against collar 101 of the inner face of top 31 of housing 22. When so configured, top end 87 of cartridge 84, carrying guide rails 98 is disposed within a substantially air-tight and fluid-tight environment within chamber 36 as is opening 92 of cartridge 84 and uppermost strip 62 is enclosed in a first position 127 shown in FIG. 4.

Once cartridge 84 is loaded, the user may use the test strips to analyze a biological fluid. Preferably, in an initial step in conducting the analysis, a fluid specimen is obtained, as for example a small amount of blood using a conventional lancing device. In order for the specimen to be analyzed, strip 62 must be made accessible so that the specimen may be applied to it. Grasping apparatus 21, the user uses a finger to engage the knurled top of tab 72 in order to move slide member 71 forwardly along slide slot 63. During forward movement of slide member 71, cam member 76, rear extension 82, and push member 116 all move forward in conjunction with tongue 73, which is coupled to slide member 71.

Forward movement along track 66 causes the lower front edge of cam member 76 to initially strike inclined leg 112 of following lip 109 carried by left face 91 of cartridge 84, shown in FIGS. 6 and 7. Continued forward movement of cam member 76 along inclined leg 112 causes compression of spring 51 within casing 48. Downward movement of cartridge 84 also breaks the moisture-resistant seal by uncoupling sealing member 97 and collar 101, shown in FIGS. 9 and 10. Continued forward movement causes lower edge of cam member 76 to engage and ride upon transverse leg 111 of following lip 109, shown in FIG. 9, holding cartridge 84 in the lowered, or unsealed, position, shown in FIG. 10.

Figure 8:
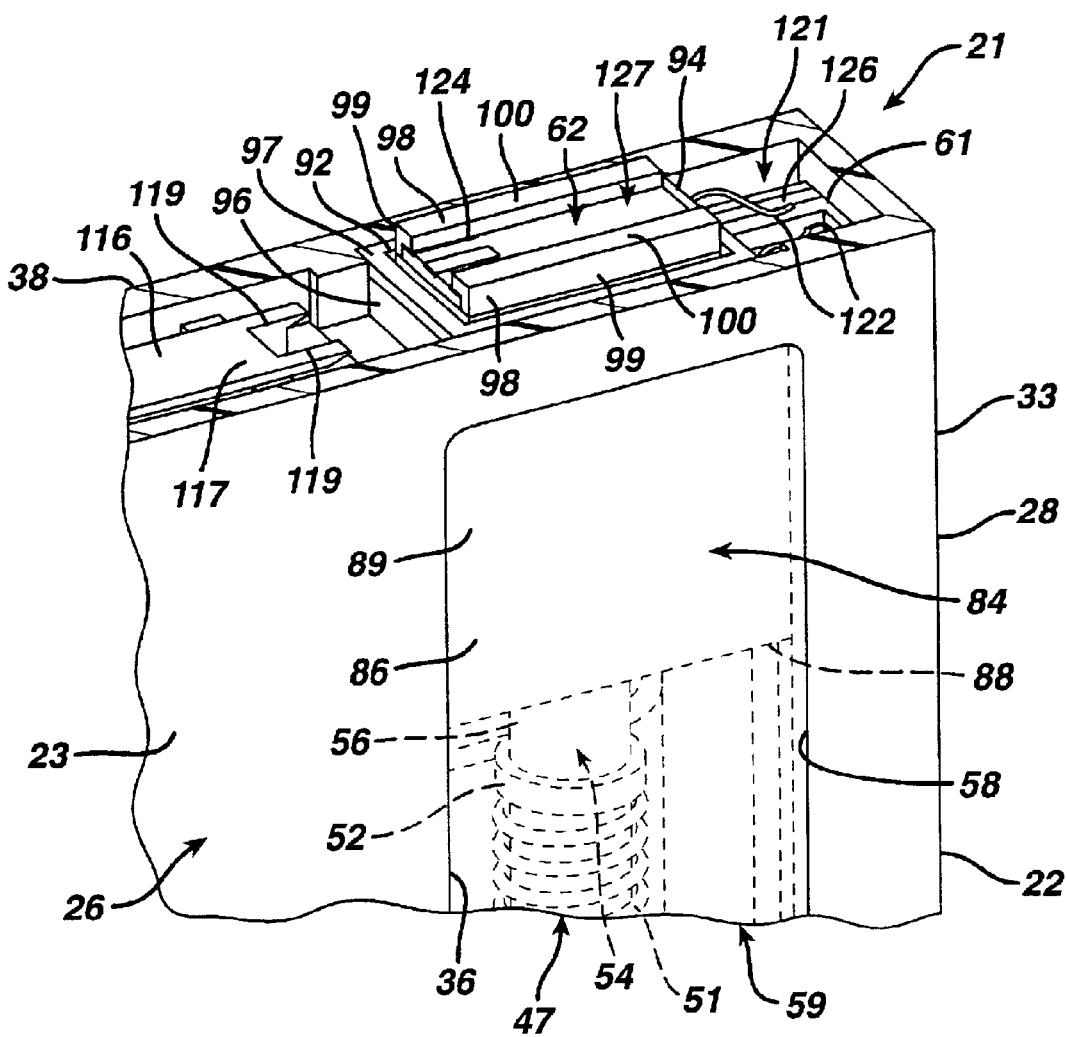
FIG. 8 is an enlarged perspective view with a partial cut-away showing the cartridge in the first position.
Figure 11:
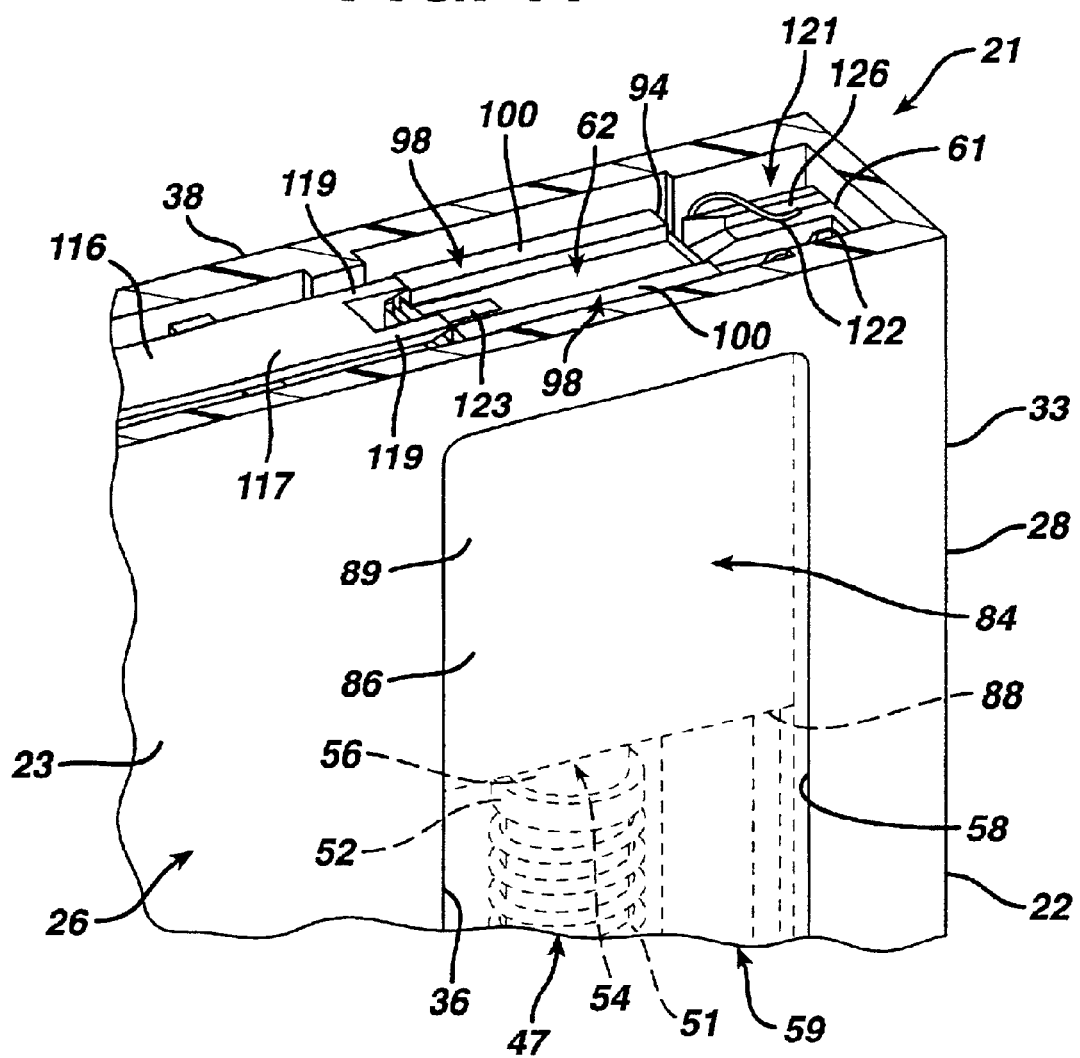
FIG. 11 is an enlarged, perspective view depicting the cartridge between the first and the second position.

Simultaneously with the forward movement of slide member 71, push member 116 moves forward until, as it approaches rear end 96 of cartridge 84, tines 119 carried thereby engage upright legs 100 and 99 of strip guide rails 98 thereby engaging the rear edge of uppermost strip 62 retained in cartridge 84, as shown in FIGS. 8, 11, and 22. Continued forward movement of slide member 71 causes strip 62 to be ejected from cartridge 84 and to assume a second position 128, shown in FIGS. 12 and 13, with the rear extremity thereof being disposed fully forward of and clear the front end of cartridge 84. In this second, or testing, position 128, each contact segment 126 of electrode 122 of meter 121 contacts working and reference electrodes 123 and 124 at the rear extremity of strip 62 as shown in FIG. 13.

After strip 62 is advanced to the second position 128, the user releases finger tab 72 whereupon spring 78 coupled to rear extremity 81 of cam member 76 urges can member 76, slide member 71, and finger tab 72 rearwardly. As cam member 76 slides rearwardly, first along transverse leg 111 and subsequently along inclined leg 112 of lip 109, plunger 54 becomes free to urge cartridge 84 upwardly whereby sealing member 97 and collar 101 are re-coupled to form the moisture-resistant seal.

Figure 12:
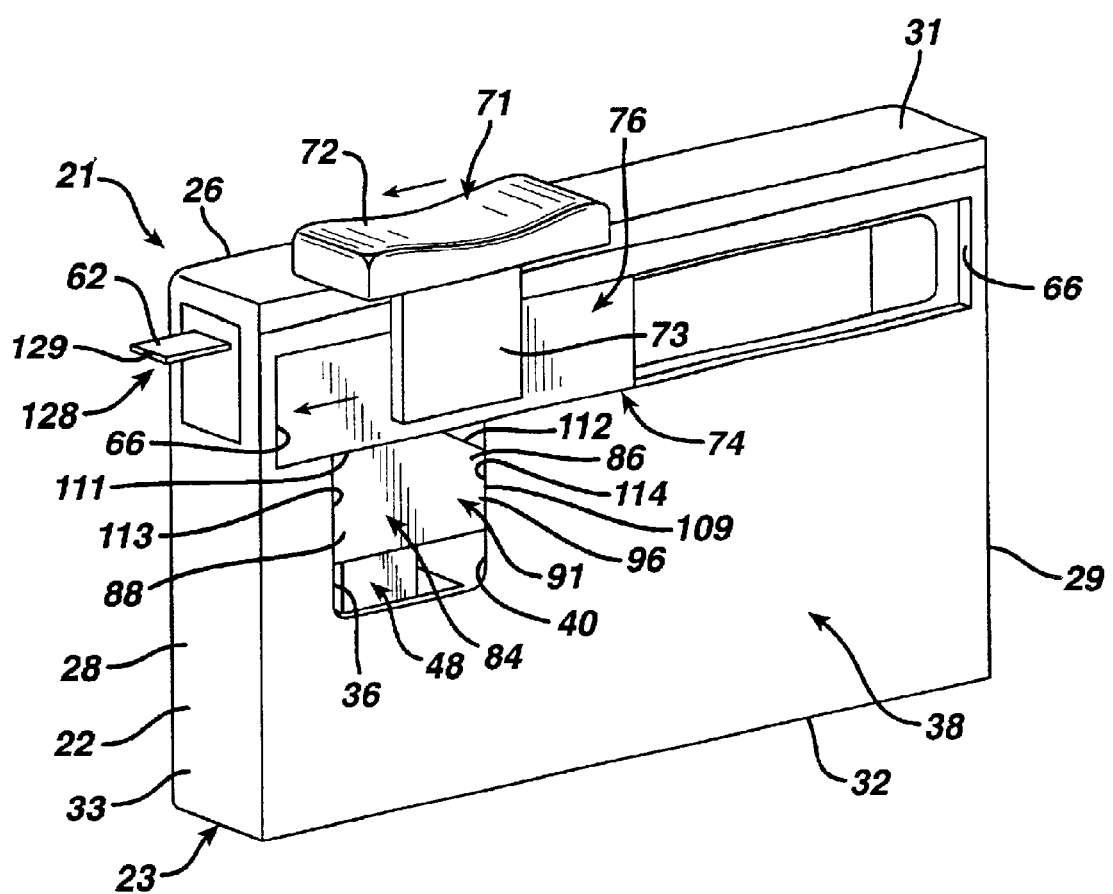
FIG. 12 is a perspective view of the right half of the apparatus of FIG. 1 showing the slide member and cartridge in the second position.

A drop of the fluid to be analyzed, for example blood, is placed onto deposition area 129 of strip 62. Alternatively, and preferably, the meter with a strip protruding therefrom as shown in FIG. 12, is brought into contact with the blood. The blood sample wicks toward the zone on the strip at which the fluid contacts the a reagent on the strip. In the case of analysis of blood for glucose levels, the strip reagent includes an enzyme for oxidizing glucose, including without limitation glucose oxidase dehydrogenase, and a redox mediator, including without limitation ferri- or ferrocyanide. Contacting of the blood plasma with the reagent results in a reaction in which the glucose is oxidized and the mediator is reduced. An electric potential difference is then applied between electrodes 123 and 124 of the strip and the resulting current is measured. The glucose level thus measured typically is shown via an LED display, which in the apparatus of the invention may be on one of the front or rear wall 26 and 27, respectively.

Once testing is completed, the test strip may be physically removed from apparatus 21 by the user. Alternatively, and preferably, means for ejecting the strip may be provided. For example, means may be provided by which forward or rearward action of the slide member fully ejects the strip from apparatus 21.

Figure 16:
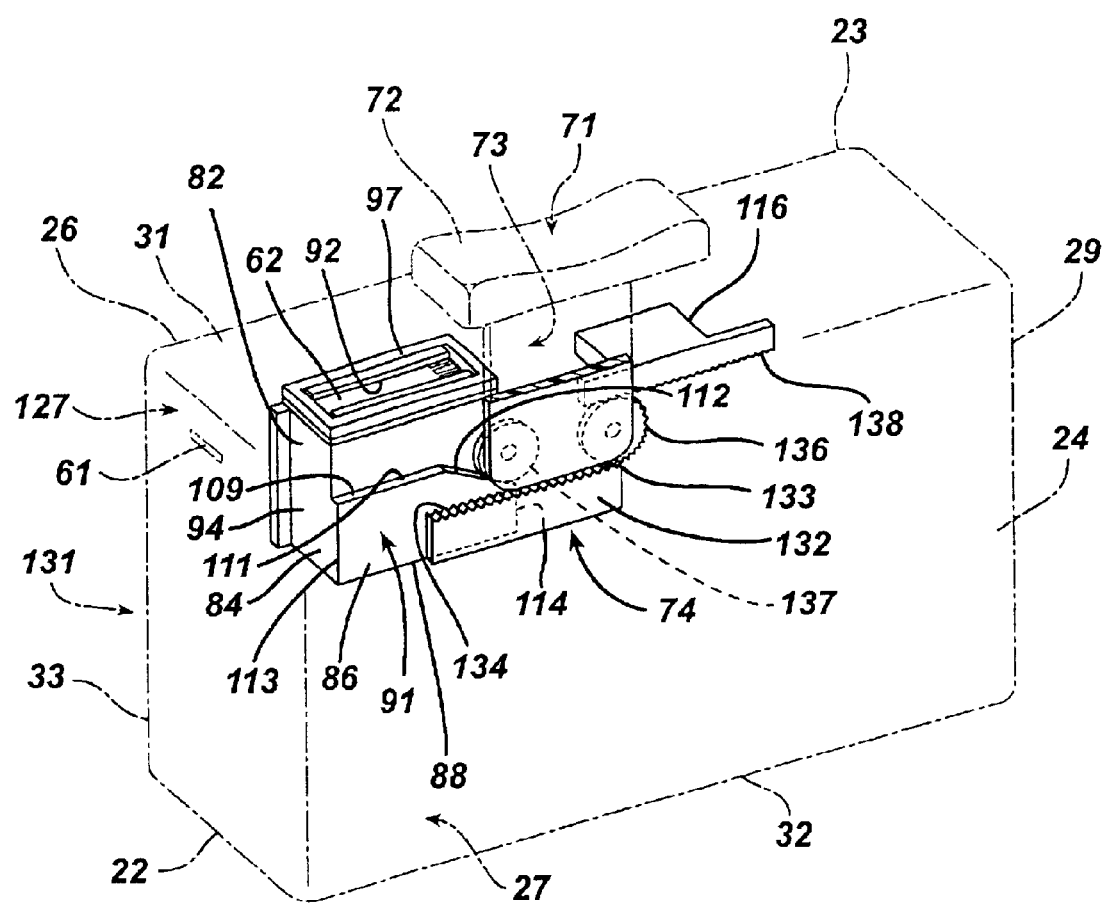
FIG. 16 is a perspective view showing another embodiment of the apparatus of the invention with the slide member and cartridge in a first position.
Figure 17:
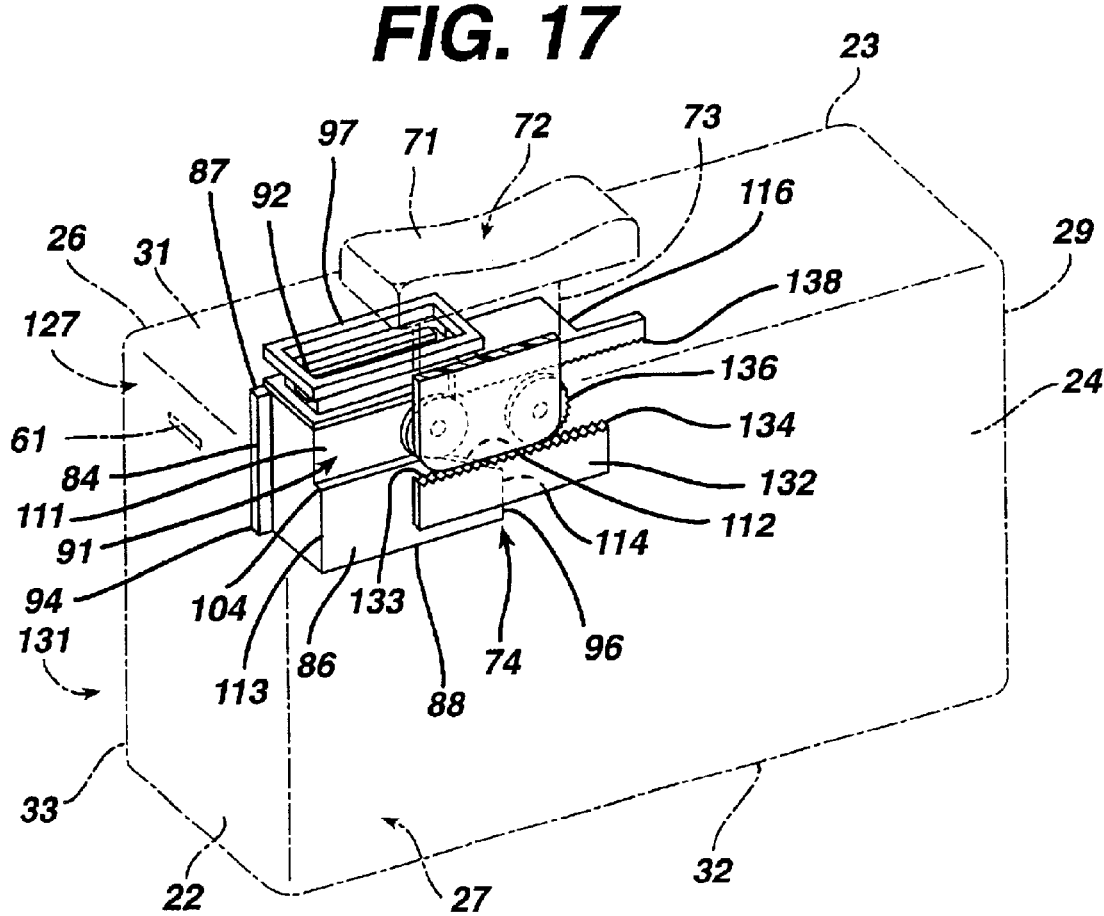
FIG. 17 is a perspective view showing the cartridge and slide member of the apparatus of FIG. 16 between the first and a second position.
Figure 18:
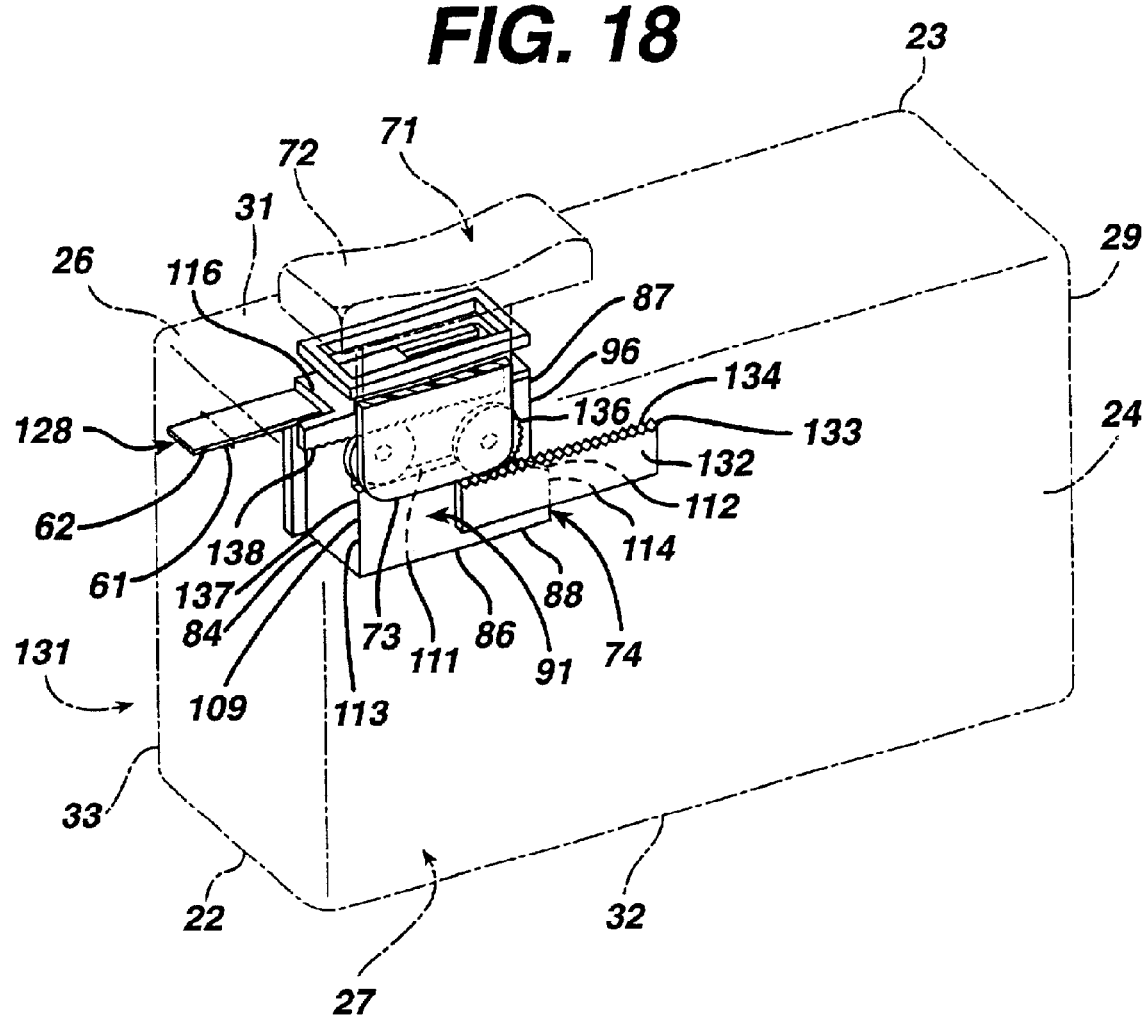
FIG. 18 is a perspective view showing the apparatus of FIG. 16 with the cartridge, slide member and strip in the second position.

An alternative embodiment of the invention is shown in FIGS. 16 through 18 in which apparatus 131 is seen, which apparatus differs from apparatus 21 in the slide and push member mechanisms used. Apparatus 131 is advantageous in that it provides a loner strip motion for the same input motion versus apparatus 21. This permits use of longer test strips that can be made to protrude farther out of the meter, making it easier for the operator to bring the strip in contact with the specimen. However, as evident from the following description, the slide and push mechanisms of apparatus 131 are more complicated than that of 21.

Apparatus 131 includes a gear rail rack or gear rack 132 either formed integral to or carried by the left face of medial wall 38 and being secured thereto in any convenient manner. Rack 132 preferably is rectangular in configuration and extends horizontally along a longitudinal axis with the front end being situated rearwardly from front wall 28 by an appropriate distance. The upper edge 133 of rack 132 is provided with gear teeth 134 extending the length thereof, as shown in FIG. 16.

In lieu of cam member 76, gear wheel 136 is carried by, and rotatably coupled to, tongue 73 of slide member 71. Gear wheel 136 has a thickness approximating that of gear rack 132 so that it meshes with, or engages, rack 132. In addition, a second cam, wheel 137 is carried by and rotatably coupled to tongue 73 forward of gear wheel 136. Cam wheel 137 is toothless and has a thickness approximating the width of cam following lip 109.

Push member 116 is provided with teeth 138 on the underside thereof. Teeth 138 also mesh with gear wheel 136 so that movement of slide member 71 causes gear wheel 136 to move along rack 132 causing translational movement of push member 116 in the same direction and at twice the speed as slide member 71.

The operation of apparatus 131 may now be described in conjunction with FIGS. 16 through 18. When tab 72 and tongue 73 are advanced in a forward direction, gear wheel 136 rotates on tongue 73 in the same direction guided by gear rack 132 with which it remains enmeshed. During advancement along gear rack 132, rotation of gear wheel 136 is transmitted to push member 116 by teeth 138. As a result, push member 116 advances translationally at twice the rate of slide member 71. With continued forward movement of slide member 71, cam wheel 137 contacts inclined leg 112 of cam following lip 109 causing cartridge 84 to be urged downwardly. The remainder of the operation of apparatus 131 is as described in conjunction with apparatus 21.

Figure 19:
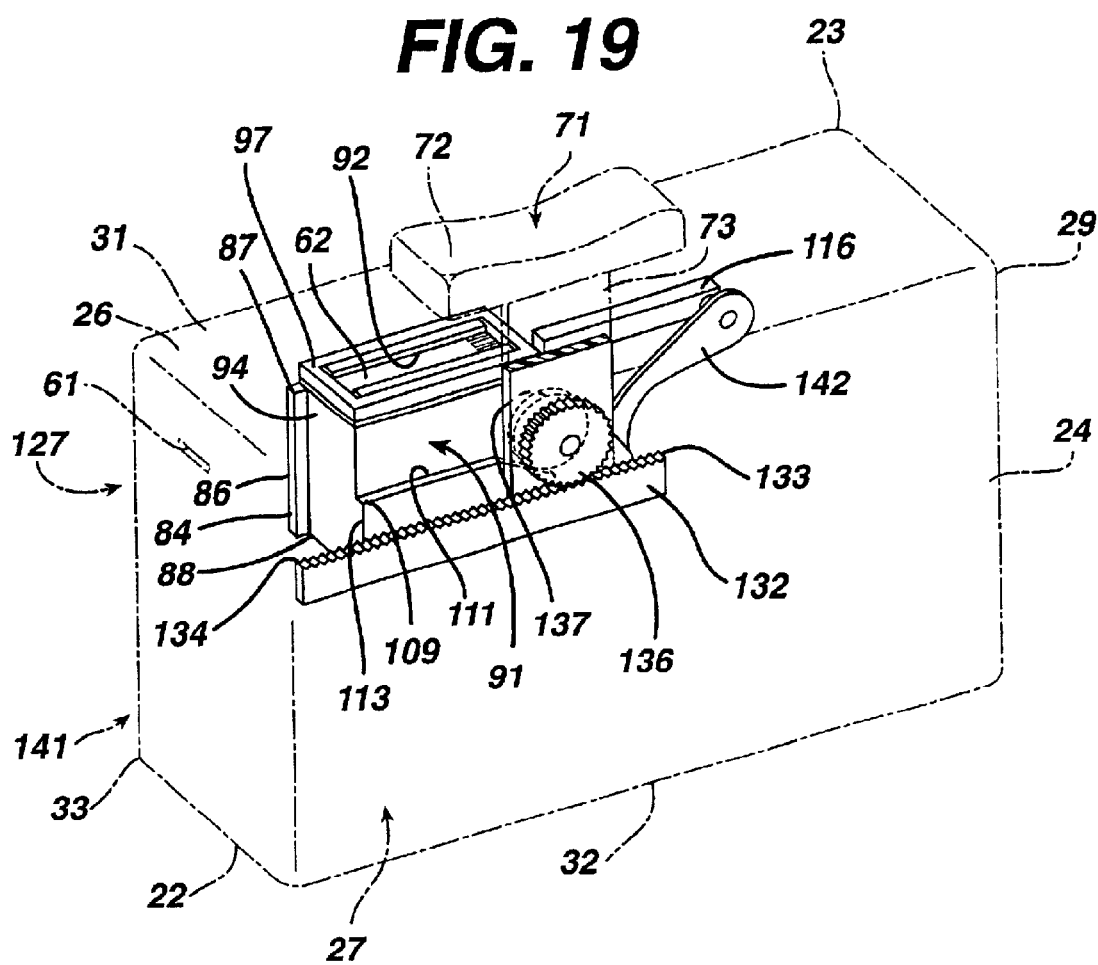
FIG. 19 is perspective view of another embodiment of the apparatus of the invention showing the cartridge and slide member in a first position.
Figure 20:
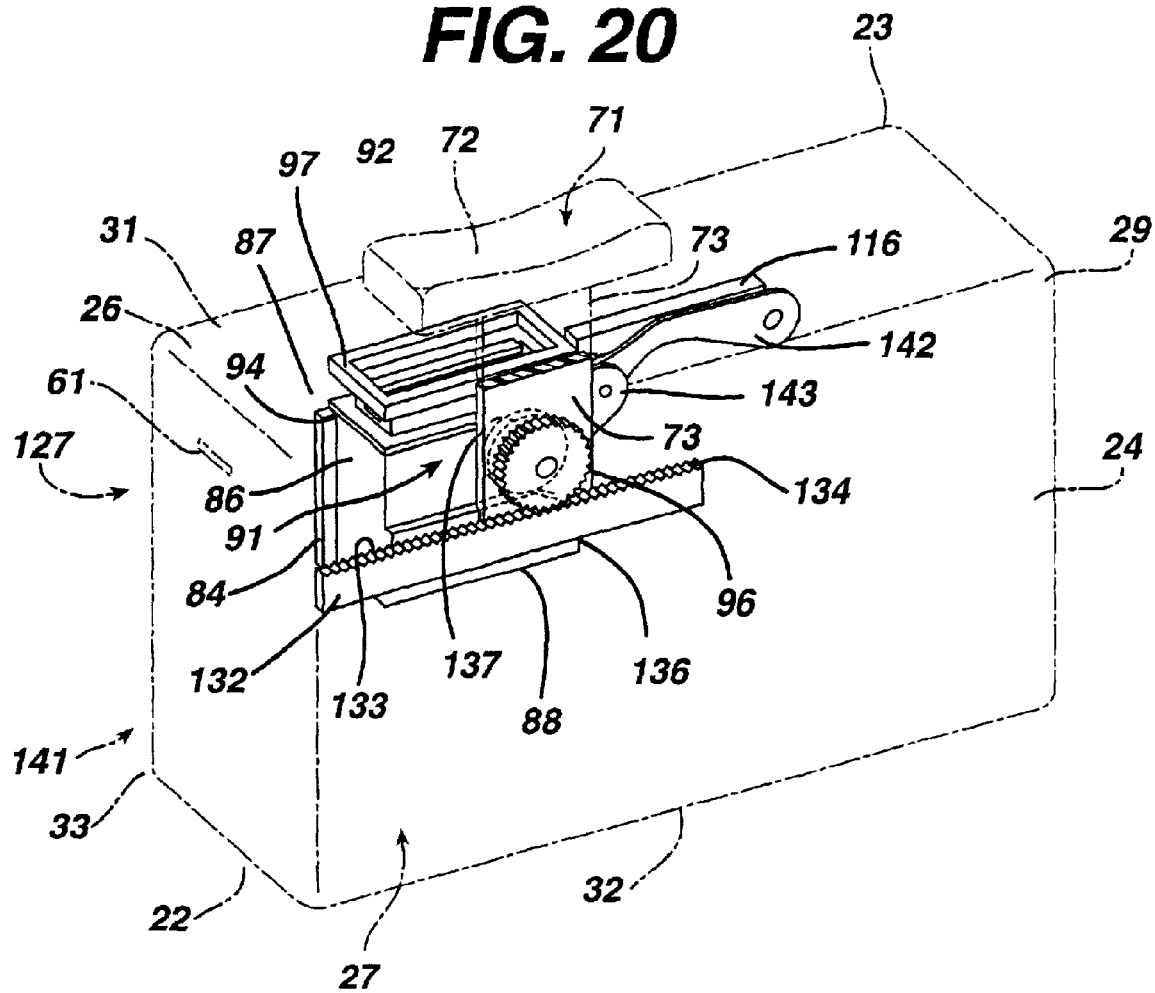
FIG. 20 is a perspective view of the apparatus of FIG. 19 showing the cartridge and slide member between the first and a second position.
Figure 21:
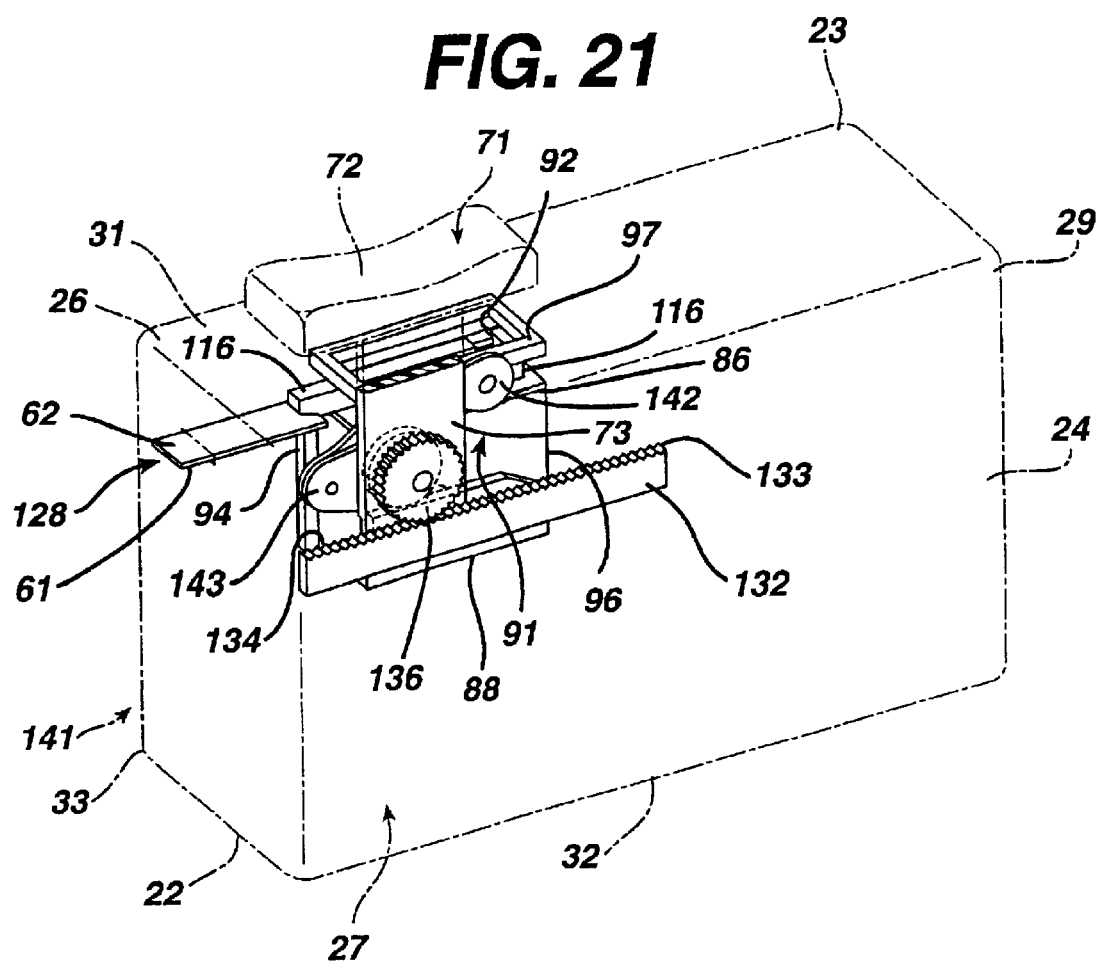
FIG. 21 is a perspective view of the apparatus of FIG. 19 showing the cartridge, slide member, and strip on the second position.

Another embodiment of the invention is depicted as apparatus 141 in FIGS. 19 through 21. In this embodiment, cam wheel 137 is mounted coaxially with gear wheel 136. Instead of gear wheel 136 being enmeshed directly to push member 116, in this embodiment cam wheel 137 includes an arm 143 swivelably coupled to link 142 which in turn is swivelably coupled to push member 116. Arm 143 and link 142 are configured to be of a size and shape whereby, similar to apparatus 131, for a given translational movement of slide member 71, the push member 116 is provided with a greater translational movement.

Figure 23:
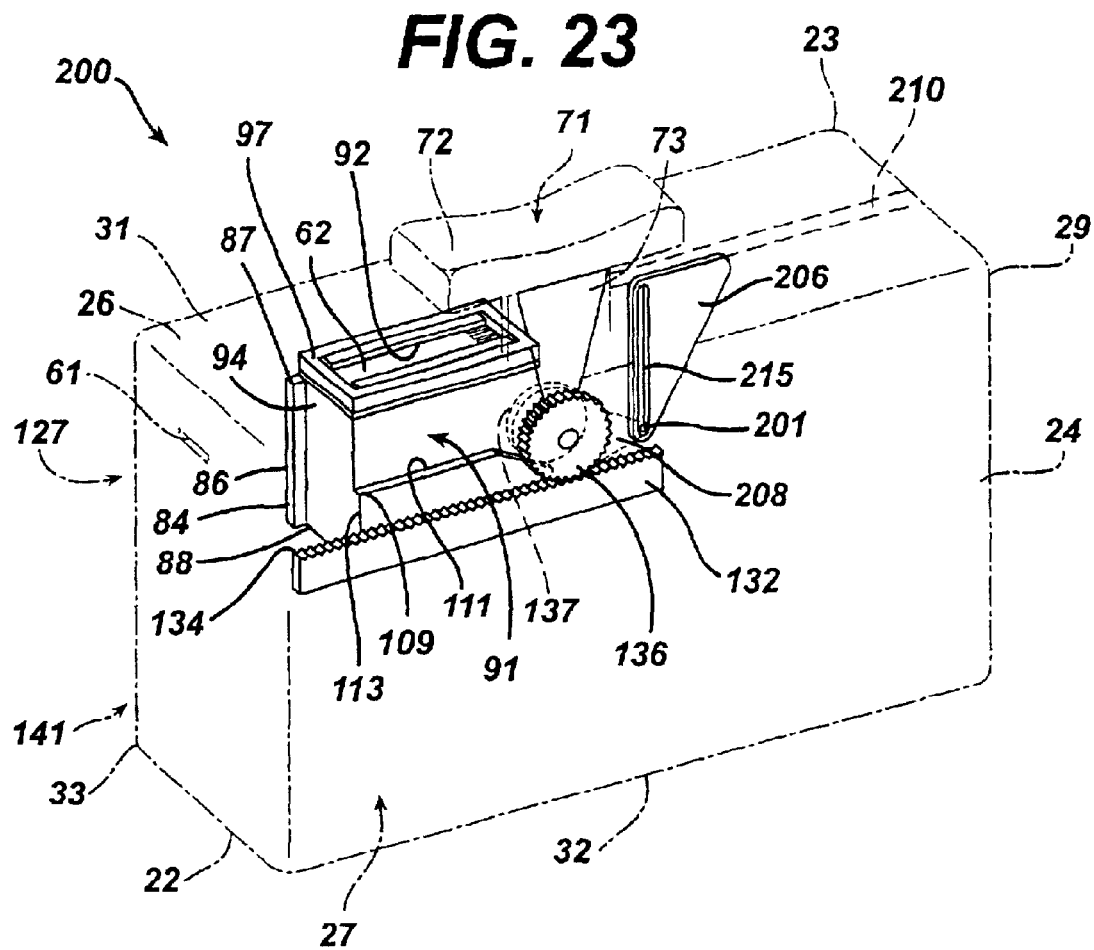
FIG. 23 is a perspective view of another embodiment of the apparatus of the invention showing the cartridge and slide member in a first position.
Figure 24:
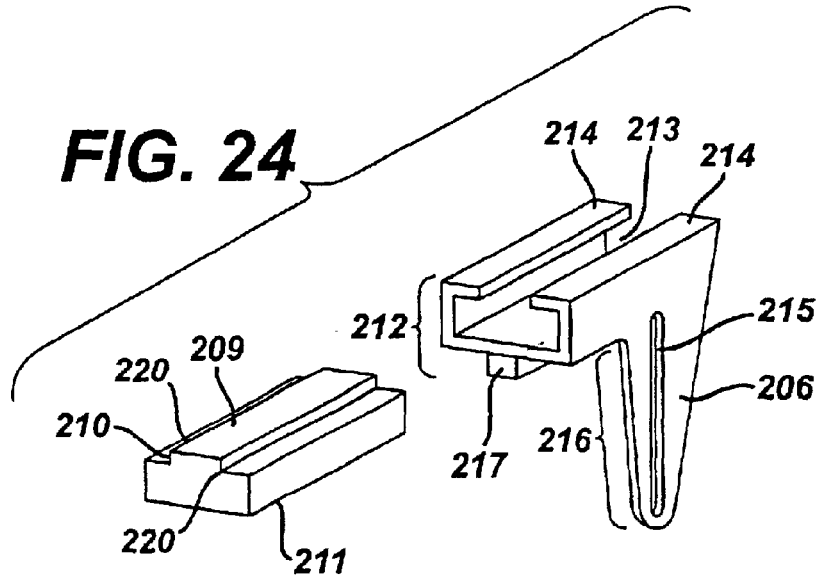
FIG. 24 is an exploded view of the push member mechanism of the embodiment of FIG. 23.

Yet another embodiment of the invention is shown in FIGS. 23 through 25, which embodiment differs from those above-described in the push member used. This embodiment is advantageous in that it provides a long strip motion for the same input motion when compared to apparatus 21 and also increases the translational movement of the push member. This permits the size of the apparatus to be decreased while increasing the ease of use, particularly for users with impaired hand use.

In FIG. 23 is shown apparatus 200 including slide member 71 and gear rack 132 as described above. As with the embodiment of FIGS. 19 through 21, a toothless cam wheel 137 is mounted coaxially with gear wheel 136 and cam wheel 137 includes arm 208. However, arm 208 is coupled to push member 206 by pin 201. Pin 201 is spaced apart a distance from the center of cam wheel 137 so that pin 201 moves in a cycloidal manner when toothless cam wheel 137 is rotatably moved forward by forward movement of slide member 71.

As shown in FIG. 23, push member 206 is associated with the inner surface of top 31 and, more particularly, is slidably coupled to push member rail 210, shown in FIG. 23 in phantom and enlarged in FIG. 24, where push member rail 210 is associated with the inner surface of top 31. Push member rail 210 has a length greater than the length of slot 63 and typically will have a length greater than the length of slot 63 by about 2 times or more so that push member 206 travels a greater distance than does slide member 71.

FIG. 24 shows an exploded view of push member 206 and push member rail 210. As shown, push member rail 210 includes top portion 209 and bottom portion 211 having rails or ledges 220 positioned therebetween for engagement of push member 206 where top portion 210 is associated with the inner surface of top 31. Top portion 210 may be associated with the inner surface of top 31 by any convenient means including, without limitation, suitable chemical, physical and mechanical means. Ledges 220 of push member rail 210 are, in turn, associated with push member 206 such that push member 206 slides along ledges 220 when slide member 71 is forwardly moved, as described in greater detail below.

As shown in FIG. 24, push member 206 has top portion 212 including a groove 213 and rails or lips 214. Top portion 212 is configured to slidably engage push member rail 210 and, more specifically, ledges 220, as above-described. Bottom portion 216 of push member 206 includes a slot 215 along which pin 201 of toothwheel cam wheel 137 slidably travels when slide member 71 is moved forwardly. The slidable travel causes push member 206 to be translationally moved. Lower front edge 217 of push member 206 is configured to engage the rear edge of an uppermost strip 62 retained in cartridge 84.

Figure 25A:
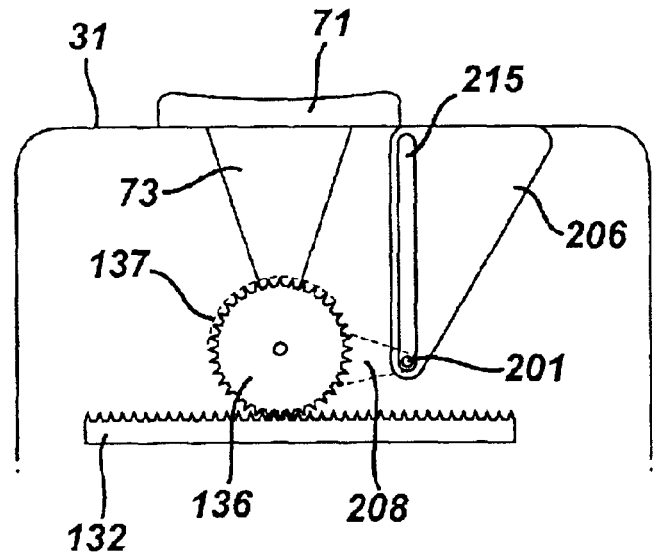
FIGS. 25a through 25d are cutaway views of the apparatus of FIG. 23 showing the progression of the push member mechanism and associated components of FIG. 23 moving forward from a first position to a second position.
Figure 25B:
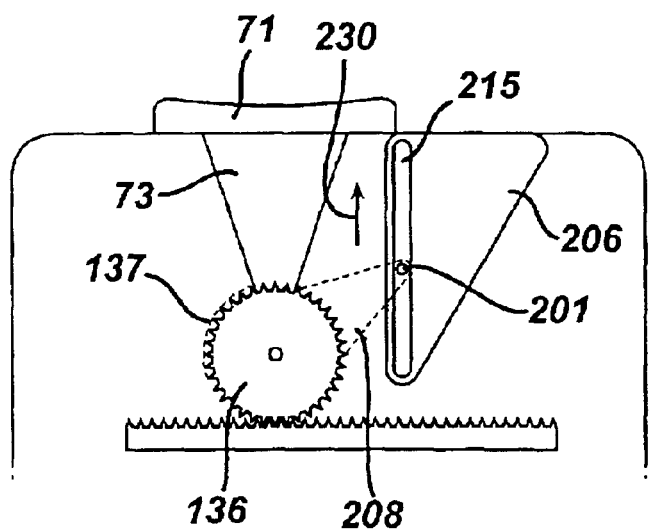

Referring to FIGS. 25a through 25d the relative positioning of portions of the apparatus 200 when slide member 71 is moved forwardly are shown. Cartridge 84, shown in FIG. 2b, is loaded within apparatus 200. Once cartridge 84 is loaded, the user grasps apparatus 200 and, with a finger engages slide member 71 and slides it forwardly. Before slide member 71 is moved forwardly, toothless cam wheel 137 is positioned so that pin 201 is engaged in the lowermost portion of slot 215 of push member 296, as shown in FIGS. 23 and 25a. As slide member 71 is forwardly moved and coupled gear wheel 136 is rotationally forwardly moved along gear rack 132, as shown in FIG. 25b, toothless cam wheel 137 also is rotationally forwardly moved. The rotational forward movement of cam wheel 137 slidably moves pin 201 upwardly along slot 215 or in the direction of arrow 230 which translationally moves push member 205 forwardly. Due to the cylcodial movement of pin 201, push member 205 is initially moved forward relatively slowly until pin 201 is forwardly rotated about 45° relative to the first position and as shown in FIG. 25b. At this position, toothless cam wheel 137 is caused to contact inclined leg 112 causing cartridge 84 to be downwardly urged as described above in reference to apparatuses 131 and 141.

Figure 25C:
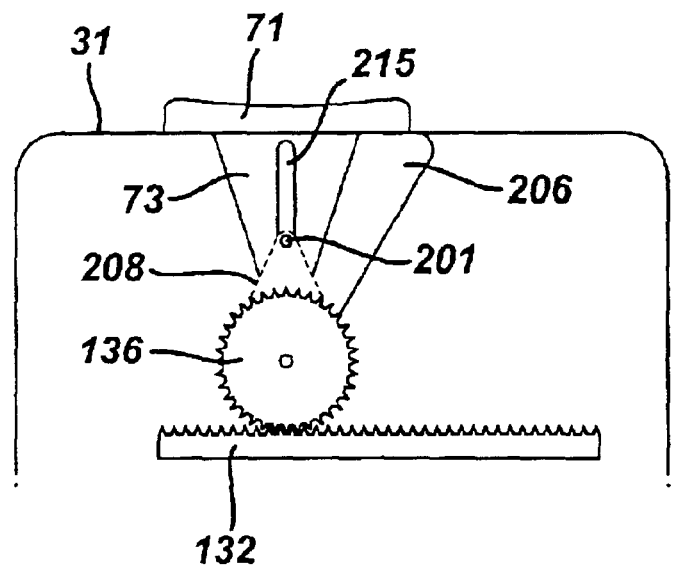
Figure 25D:
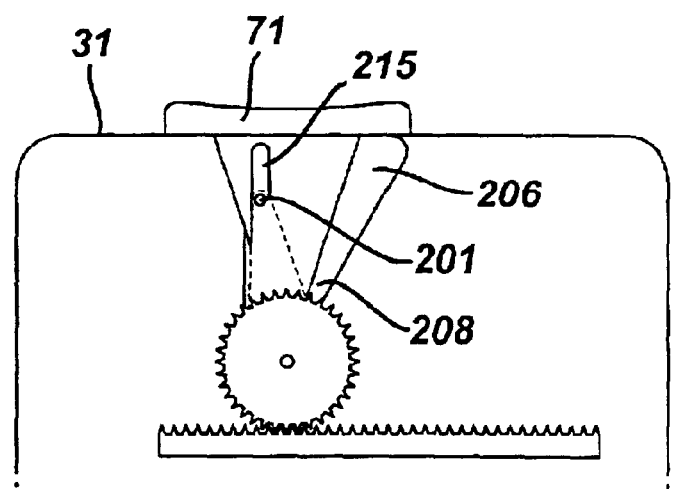

As push member 206 continues to be moved translationally forward beyond the 45° angled position, shown in FIGS. 25c and 25d, the rate of the translational movement of push member 206 is increased relative to the rate of translational movement before or prior to the time the 45° position of pin 201 is reached. Once cartridge 84 has been downwardly urged by toothless cam wheel 137, continued forward movement of toothless cam wheel 137 translationally moves push member 206 more quickly than previously moved. Continued forward movement of slide member 71 and, thus, toothless cam wheel 137 and push member 206, causes lower front edge 217 of push member 206 to engage the rear edge of an uppermost strip 62 retained in cartridge 84. Continued forward movement causes the engaged strip to be ejected from cartridge 84 to assume a second position for testing as above-described.

What is claimed is:

1. An apparatus comprising:
   a dispenser comprising a housing having a chamber; a means for retaining a plurality of test strips in a substantially moisture-proof, air-tight first position; and a means for opening the chamber and moving one of the plurality of test strips translationally from a first position inside of the chamber to a second position at least partially outside of the chamber, wherein the opening of the chamber and the moving of the one test strip is achieved by a single mechanical motion; and
   an electrochemical analyzing means for analyzing a biological fluid.

2. The apparatus of claim 1, wherein the housing further comprises:
   a sealing member;
   a circumferential collar;
   a dispensing outlet; and
   an urging means for urging the test strip retaining means.

3. The apparatus of claim 2, wherein the means for opening the chamber and moving one of the plurality of test strips further comprises:
   a slide member;
   a cam member integral with the slide member; and
   a push member integral with the slide member.

4. The apparatus of claim 1, wherein the housing further comprises a gear rack.

5. The apparatus of claim 4, the means for opening the chamber and moving one of the plurality of test strips further comprises:
   a slide member;
   a gear wheel rotatably coupled to the slide member and enagageable with the gear rack;
   a cam wheel rotatably coupled to the slide member; and
   a push member with a plurality of teeth suitable for meshing with the gear wheel.

6. The apparatus of claim 4, wherein the means for opening the chamber and moving one of the plurality of test strips further comprises:
   a slide member;
   a gear wheel rotatably coupled to the slide member and engageable with the gear rack;
   a push member;
   a link swivelably coupled to the push member; and
   a cam wheel mounted coaxially with the gear wheel and comprising an arm swivelably coupled to the link.

7. The apparatus of claim 4, wherein the means for opening the chamber and moving one of the plurality of test strips further comprises:
   a slide member;
   a cam wheel rotatably coupled to the slide member;
   a gear wheel engageable with the gear rack; and
   a push member having an arm coupled thereto by a pin spaced a distance from the center of the cam wheel wherein the pin is moveable in a cycloidal manner when the cam wheel is rotatably moved.

8. An apparatus comprising:
   a dispenser comprising a housing having a chamber, a means for retaining a plurality of test strips in a substantially moisture-proof, air-tight first position, and a means for opening the chamber and moving the plurality of test strips one at a time from a first position inside of the chamber to a second position at least partially outside of the chamber; and
   an electrochemical analyzing means for analyzing a biological fluid deposited on a test strip when in the second position.

9. The apparatus of claim 8 further comprising means for ejecting the plurality of test strips from the chamber one at a time.

10. A method of dispensing and using a plurality of test strips for analyzing biological fluid, the method comprising:
   providing an apparatus comprising a housing having a chamber, a means for retaining a plurality of test strips in a substantially moisture-proof, air-tight first position within the chamber, and an electrochemical means for analyzing a biological fluid;
   opening the chamber and moving one of the plurality of test strips from the first position inside of the chamber to a second position at least partially outside of the chamber;
   causing the biological fluid to contact the test strip when in the second position; and electrochemically analyzing the biological fluid when the test strip is in the second position.

11. The method of claim 10 wherein the opening of the chamber and the moving of the one test strip is achieved by a single motion.

12. The method of claim 10 further comprising ejecting the used test strip from the chamber after analyzing the biological fluid.

* * * * *